(12) United States Patent
Van Albert et al.

(10) Patent No.: US 7,660,692 B2
(45) Date of Patent: Feb. 9, 2010

(54) BALLISTIC IMPACT DETECTION SYSTEM

(75) Inventors: Stephen A. Van Albert, Silver Spring, MD (US); Paul F. Bruney, Silver Spring, MD (US); Robert Matthews, San Diego, CA (US); Linas Kunstmanas, Valley Center, CA (US)

(73) Assignees: Quantum Applied Science & Research, Inc., San Diego, CA (US); United States of America, Washington, DC (US)

( * ) Notice: Subject to any disclaimer, the term of this patent is extended or adjusted under 35 U.S.C. 154(b) by 363 days.

(21) Appl. No.: 11/629,864

(22) PCT Filed: Jun. 16, 2005

(86) PCT No.: PCT/US2005/021195

§ 371 (c)(1),
(2), (4) Date: Dec. 18, 2006

(87) PCT Pub. No.: WO2006/085935

PCT Pub. Date: Aug. 17, 2006

(65) Prior Publication Data

US 2007/0260407 A1    Nov. 8, 2007

Related U.S. Application Data

(60) Provisional application No. 60/581,975, filed on Jun. 16, 2004.

(51) Int. Cl.
*G01D 1/00* (2006.01)
*G06F 19/00* (2006.01)

(52) U.S. Cl. .................................................. 702/127

(58) Field of Classification Search ................ 702/127, 702/33–36, 66, 189, 41, 56; 73/12.01, 12.04
See application file for complete search history.

(56) References Cited

U.S. PATENT DOCUMENTS

| | | | | |
|---|---|---|---|---|
| 4,305,142 A | * | 12/1981 | Springer | ..................... 367/127 |
| 4,349,728 A | * | 9/1982 | Phillips et al. | .............. 235/400 |
| 4,413,202 A | | 11/1983 | Krempl et al. | |
| 4,761,005 A | * | 8/1988 | French et al. | ................ 273/454 |
| 5,925,972 A | * | 7/1999 | Shrader et al. | .............. 310/338 |
| 6,349,201 B1 | * | 2/2002 | Ford | ........................ 455/404.1 |
| 6,411,195 B1 | * | 6/2002 | Goldman | ..................... 340/5.1 |

(Continued)

OTHER PUBLICATIONS

United States Army White Paper, "Concepts for the Objective Force", Oct. 1999.

(Continued)

*Primary Examiner*—Michael P. Nghiem
*Assistant Examiner*—Cindy H Khuu
(74) *Attorney, Agent, or Firm*—Diederiks & Whitelaw, PLC

(57) ABSTRACT

A wearable ballistic impact protection system detects impacts to a body. The system includes multiple sensors for detecting vibration. The sensed vibrations are converted to electrical signals which are filtered. Electronic components are provided to determine whether the filtered signal have frequency and amplitude characteristics of impact that cause injury to a body. Preferably, the sensors are Piezo-electric film sensing elements. Information regarding the extent of the impact and injuries to the body may be transmitted to a remote location so that medics or other personnel may be informed to the extent of injuries to the body so that they may provide medical assistance.

18 Claims, 30 Drawing Sheets

U.S. PATENT DOCUMENTS

| | | |
|---|---|---|
| 6,769,286 B2 | 8/2004 | Biermann et al. |
| 6,930,608 B2 * | 8/2005 | Grajales et al. .......... 340/573.5 |
| 7,174,277 B2 | 2/2007 | Vock et al. |
| 7,516,643 B2 * | 4/2009 | Valentini .................. 73/12.01 |
| 2002/0043106 A1 * | 4/2002 | Board ......................... 73/579 |
| 2002/0180605 A1 | 12/2002 | Ozguz et al. |
| 2005/0067816 A1 * | 3/2005 | Buckman ................ 280/730.1 |
| 2005/0096513 A1 | 5/2005 | Ozguz et al. |
| 2005/0225443 A1 * | 10/2005 | Lerg ...................... 340/539.13 |
| 2006/0161356 A1 * | 7/2006 | Desroses et al. ............. 702/41 |
| 2007/0089480 A1 * | 4/2007 | Beck ......................... 73/12.01 |

OTHER PUBLICATIONS

Bellamy, R.F., "The Causes of Death in Conventional Land Warfare: Implications for Combat Casualty Care Research", Military Medicine, vol. 149, pp. 55-62, Feb. 1984.

Carey, "Analysis of Wounds Incurred by U.S. Army Seventh Corps Personnel Treated in Corps Hospitals During Operation Desert Storm, Feb. 20 to Mar. 10, 1991", The Journal of Trauma Injury, Infection, and Critical Care, vol. 40, No. 3, pp. S165-S169, Mar. 1996.

* cited by examiner

BALLISTIC IMPACT DETECTION SYSTEM

CROSS-REFERENCE TO RELATED APPLICATION

The present application represents a National Stage application claiming priority of PCT/US2005/021195 filed Jun. 16, 2005 entitled "Ballistic Impact Detection System", which claims the benefit of U.S. Provisional Patent Application Ser. No. 60/581,975 filed on Jun. 16, 2004 and entitled "Ballistic Impact Detection System (BIDS)"

STATEMENT OF GOVERNMENT INTEREST

The United States Government retains a royalty fee, fully paid up, non-exclusive license to make, use, have made, or have the invention used for governmental purposes.

BACKGROUND OF THE INVENTION

1. Field of the Invention

The present invention is generally directed to ballistic impact detection systems. More particularly, the invention is directed to a wearable ballistic impact detection system for detecting impacts to a body and especially impacts which might cause injury.

2. Discussion of the Art

The future battlefield is projected to be asymmetric, non-contiguous and nonlinear. To meet the challenge of future conflicts, the U.S. Army is changing its paradigm from linear and sequential operations to simultaneous and distributed operations. Sophisticated and adaptive adversaries are making unconventional tactics, such as guerrilla warfare and terrorist attacks, commonplace. In the future, as today, ground forces will continue to be counted on to win, hold the ground and rebuild the peace. The centerpiece enabler of the Army's transformation is the Future Force Warrior (FFW). FFW is a revolutionary redesign of the individual warfighter platform from the skin out. FFW is a system wherein data from sensors on the individual soldier are fused with similar information from other soldiers in the unit of action. As the data is integrated and sent back, the warfighter becomes a sensor node in a bigger network mesh which ultimately allows battlefield commanders to quickly react to critical information. Elements of the individual warfighters health status will be incorporated into the data stream from physiological monitoring devices worn by each soldier. The Warfighter Physiological Status Monitor (WPSM) is the medical system that will deliver pertinent information that will keep the soldier in the fight and, in the event of becoming a combat casualty, aid medics in rescue and recovery operations.

The central tenet to the Army's transformation to FFW is the ability to "see first, understand first, act first and finish decisively." The underlying foundation for achieving this detect-decide-deliver goal of battlefield tactics will be information technology. Acquiring critical information and delivering it rapidly and correctly will have a profound effect on the tactical, operational and strategic success of future combat missions. In the future, the Army unit of action will conduct operations over larger spaces. This translates into small, disparate fighting groups covering far more territory with a single medic in support. It is quite likely that FFW warfighters will be out of sight and hailing distance of medics and will rely on a medical information sub-network to achieve adequate levels of medical support. Early notification of a soldier's need for medical attention can reduce the time to initial treatment and thus may reduce the morbidity and mortality of wounded soldiers.

Data from a study of causes of death from the Vietnam War shows that while 66% of combat casualties die within the first 5 minutes of being wounded, there is an opportunity to save lives if a medic can get to a soldier quickly. FIG. 1 shows the percentage of all combat deaths as a function of the time from the wounding event. A therapeutic window of opportunity exists for those soldiers killed in action (KIA) in the timeframes encompassing 5 minutes to 6 hours. Given findings during Operation Desert Storm that the predominant cause of deaths in Corps hospitals was exsanguinations from extremity wounds, it is likely that with advances in body armor, extremity wounds will become a large percentage of potentially salvageable casualties on the battlefield. Knowing when a wounding event occurs and the ability to engage other physiological apparatus on the soldier to determine the extent of the casualty will play an important role in the required remote triage capability needed to change battlefield casualty statistics.

One known way to detect penetrating impacts is to use a mesh fabric incorporating fiber optics. When a fiber is broken, it is assumed to be caused by a penetrating impact. However, such a system is fragile and cannot accurately determine a ballistic impact from a rip or tear in the fabric caused by other sources.

Regardless of potential solutions, there exists a need in the art for a wearable ballistic impact detection system for detecting impacts to a body and especially impacts which might cause injury. The over-arching goal of the Ballistic Impact Detection System (BIDS) and WPSM program is to increase survivability of the soldier on the battlefield and facilitate more rapid triage for the combat medic. The BIDS has the following advantages: it is less expensive to manufacture; it detects impacts in extremities; is not prone to false positives from rips and tears; and is able to detect non-penetrating, but injurious blast overpressure.

SUMMARY OF THE INVENTION

The Ballistic Impact Detection System (BIDS) comprises a means to detect when a human body is impacted by a potentially injurious impact, such as a bullet, shrapnel or a significant blast wave. Piezo-film sensor elements detect the acoustic vibration patterns caused by an impact and convert them to a voltage. The voltage is passed through a circuit which determines if the impact has the frequency and amplitude characteristics of impacts that cause injuries. BIDS will be integrated into the Warfighter Physiological Status Monitor (WPSM) being developed for the Future Force Warrior (FFW) program. The WPSM represents the first attempt to place physiological monitoring equipment on individual soldiers. While the overall purpose of the WPSM is to provide information as to the health of the soldier, it has two distinct modes: operational and combat casualty. The BIDS will be used as the trigger mechanism to automatically detect a potentially injurious impact. This will enable the WPSM to begin monitoring physiological signals at faster rates in order to provide the medic with information enabling remote triage. This information is also of value to command and control elements.

Two sound sensors are positioned on a combatant's body to register high-energy acoustic signatures produced by ballistic impacts. The voltage output from these sensors feeds a small battery-powered analog and/or digital circuit also carried by the combatant. The circuitry isolates these signatures according to their voltage amplitudes and frequencies and discerns the approximate impact locations on the body within right, center and left general regions. The circuitry outputs "off" or "on" signals corresponding to each of these three general locations. The "on" outputs, signifying a ballistic impact, can ultimately be interfaced to a wireless link with a medical receiver in order to provide notification that the soldier has experienced one or more wounding events in these respective locations.

The BIDS is designed to detect ballistic impacts to the soldier's body. In future Army battle scenarios, soldiers will be spread over a much larger battle zone. It is quite likely that the solder will be out of direct contact with medical personnel. BIDS will act as a trigger for other on-body systems to collect physiological data at a faster rate. This data will then be radioed to the medic to allow remote triage.

Some of the novel features of this invention include the application of Piezo-film sensors on the body that pick up skin vibrations, detection and determination of frequencies associated with a ballistic impact, determination of the location of ballistic impacts on the body, determination of wound severity and detection of blast overpressure.

Ballistic impact detection could also prove valuable to police units, firefighters and other personnel working in hazardous environments for wound detection. The BIDS can also be used to detect impact for machinery, buildings and equipment and to sense vibrations for machinery. The BIDS can be built into body armor, battle fatigue, uniforms or other garments/articles worn by an individual providing for an automatic call for help.

Additional objects, features and advantages of the present invention will become more readily apparent from the following detailed description of a preferred embodiment when taken in conjunction with the drawings wherein like reference numerals refer to corresponding parts in the several views.

DETAILED DESCRIPTION OF THE INVENTION

The BIDS design centers on reducing false-positive indications to near zero. It would be approaching impossibility to completely rule out false-positive indications due to the number of 'normal' tests on all body types necessary. Because the BIDS is soldier-born, there are always requirements of near-zero cube, weight and power. An analog based system was designed based on the proof-of-concept data. Testing from the proof-of-concept phase indicates that discrimination is achieved by isolating frequencies in the 400-1000 Hertz band. If these frequencies meet a threshold voltage requirement, an impact criterion is met. While high velocity swine tests corroborate the earlier proof-of-concept tests in terms of the frequency range of interest, preferably a high-pass filter is employed for the circuit.

The circuitry for BIDS is either purely digital in nature or an analog-digital hybrid. In a preferred embodiment, the circuitry is primarily analog with a digital output that is compatible with computing devices. The BIDS includes two sensors that couple to the body in such a way as to sense the vibrations of the skin. The sensors are Piezo-film mounted on a flexible substrate of Mylar plastic. The vibrations produce voltages commensurate to the frequency and amplitude of the vibrations. Each sensor signal is processed in similar circuit sections. All sensor signals are ultimately fed into logic circuitry that makes a determination as to the location of the impact.

Figure 2:
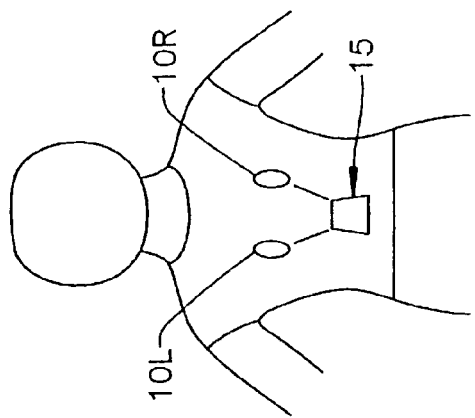
FIG. 2 is a diagram showing sensors placed on a human body in accordance with the invention.
Figure 1:
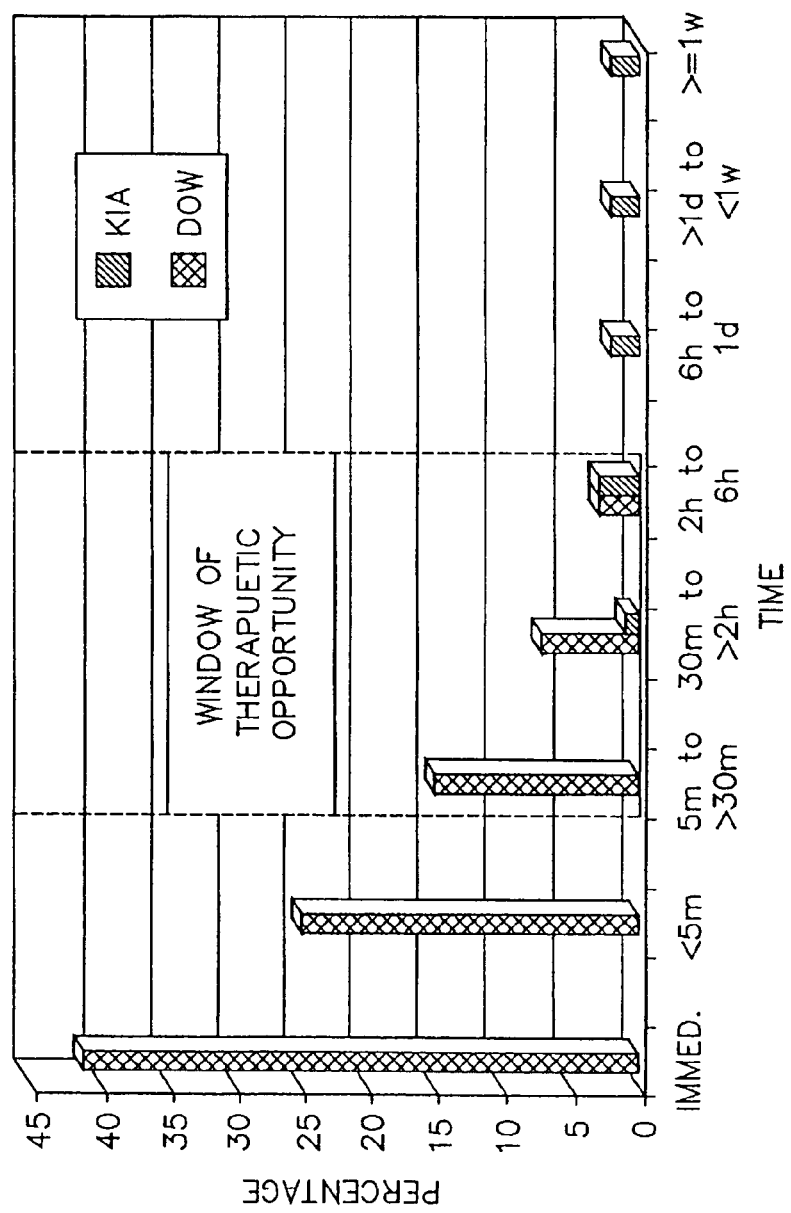
FIG. 1 is a graph showing the percentage of total combat deaths as a function of time from a wounding event during the Vietnam war.

Turning now to FIG. 2, there is shown the placement of sensors 10L and 10R on a human body connected to the various group of electronics 15 which make up the Ballistic Impact Detection System. Of course, in this case, the body is shown from the rear so that 10L represents the left sensor and 10R represents the right sensor. It should be noted that, although two sensors are shown here, numerous different types and numbers of sensors could be used. The sensors 10L or the electronics 15 may be mounted on a bullet proof vest, body armor, battle fatigues, a uniform or other garments/articles designed for the body. The electronics 15 may include a transmitter to transmit information to a remote location.

Such a transmitter is disclosed in U.S. Pat. No. 6,349,201 which is incorporated herein by reference.

Figure 3:
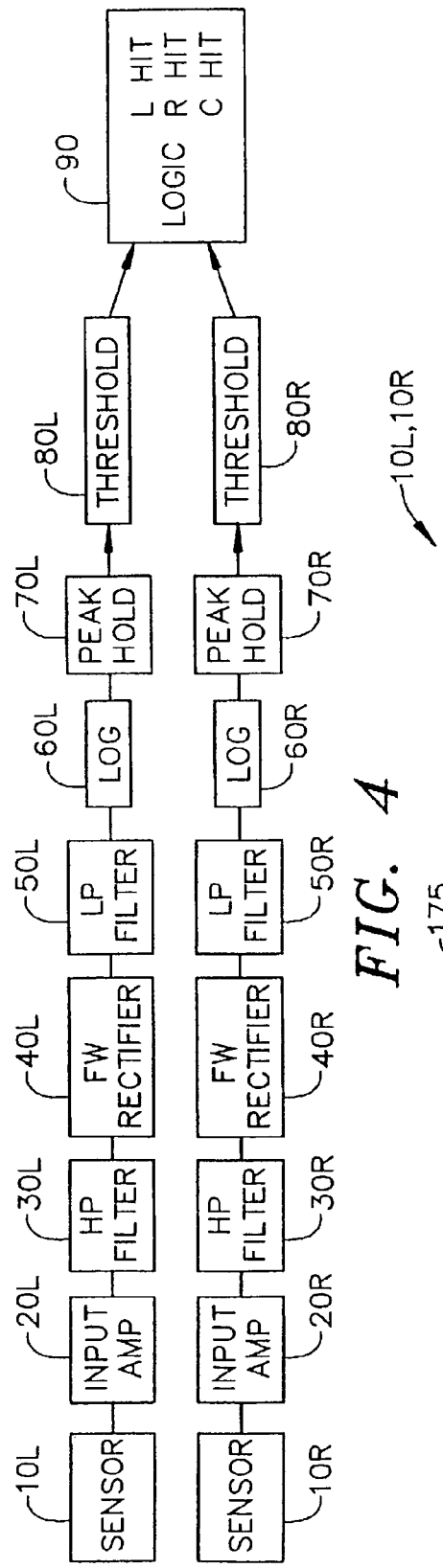
FIG. 3 is a schematic view of the overall arrangement of the ballistic impact detection system according to a preferred embodiment of the invention.

Turning now to FIG. 3, there is shown left and right channels of electronics which lead to a logic circuit. The left channel starting with sensor 10L is shown in parallel with the right channel beginning with sensor 10R. Since both channels are correspondingly constructed, only one channel needs to be discussed below. The voltage signal from sensor 10L is conducted to an input buffer amplifier 20L. The signal then passes through a high pass filter 30L. The current embodiment uses a 3-pole Bessel with a cutoff frequency of 5000 Hertz. While much of the work to date indicates that telltale frequencies exist in to 400-1000 Hertz range, it is impossible to create an analog filter with such a narrow band pass. The 5000 Hertz filter is 42 dB down at 1000 Hertz and 60 dB down at 500 Hertz. It has been found that there is enough frequency information passed by this filter to adequately discriminate the impact signals collected. The signal is then conducted to a full-wave rectifier 40L which converts the voltage from bipolar to only positive. The signal then passes through a 3-pole 1000 Hertz low pass filter 50L which widens the voltage peaks of interest. The signal is then conducted into a logarithmic amplifier 60L. The output of amplifier 60L is a voltage equal to the log of the input voltage. This stage at amplifier 60L prevents a large signal from saturating the next stages. Saturation would cause loss of frequency information that could lead to false-positive impact determinations. The next stage is a peak hold circuit 70L which determines and conducts the peak voltage in the signal to the threshold circuit stage 80L. Threshold circuit stage 80L compares the peak voltage of the signal to a threshold voltage. If the signal voltage is higher than the threshold, then an impact has occurred. The original signal voltage is passed to logic 90 that determines location. This location logic 90 compares the amplitudes of all the sensors to make a location determination.

Figure 4:
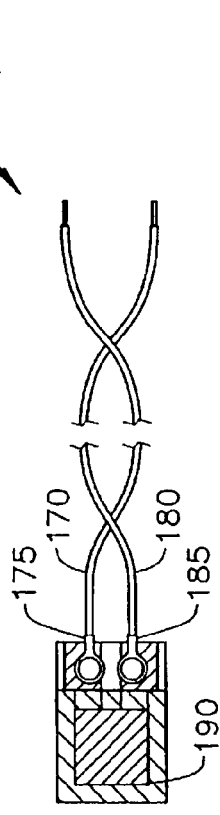
FIG. 4 is a cross-sectional view of a sensor used in the ballistic impact detection system.
Figure 5:
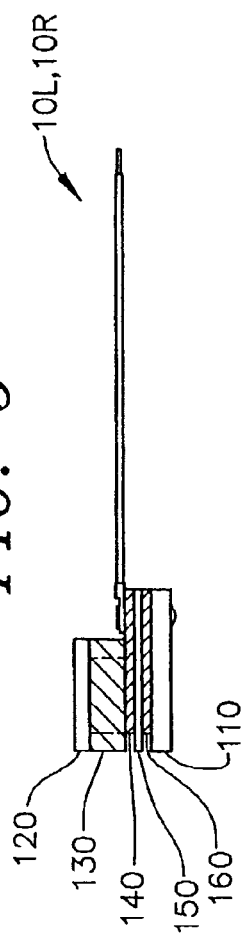
FIG. 5 is a side view of the sensor shown in FIG. 4.

Turning now to FIGS. 4 and 5, there is shown a sensor 10 which could be either of sensors 10L or 10R described above. This particular sensor is a Piezoelectric-film type sensor generally formed of a Piezoelectric-polymer such as polyvinylidene-floride (PVDF). Such a sensor has a base layer 110 preferably formed of approximately 14 mil thick Mylar and a top layer 120 formed of approximately 7 mil thick Mylar. Between the two outer Mylar layers 110 and 120, there are formed, in order: a layer 130 of approximately 1/16" thick foam, which is located below Mylar layer 120; a metal silver ink layer 140 forming the negative terminal of sensor 10; a PVDF layer 150; and a positive silver ink layer 160. Although not shown, each sensor 10L, 10R preferably incorporates FET circuitry.

The negative silver ink layer 140 and the positive silver ink layer 160 are connected to output wires 170 and 180 by means of eyelet connectors 175 and 185, respectively. All of the layers mentioned above are preferably laminated together, such as with an approximately 1 mil acrylic adhesive. The overall capacitance for such a sensor is preferably 550 Picofarads, with a dissipation factor of less than 0.025. Sensors 10L and 10R could be constructed in other ways, such as those shown in U.S. Pat. Nos. 4,413,202 and 4,761,005 which are incorporated herein by reference.

Figure 6:
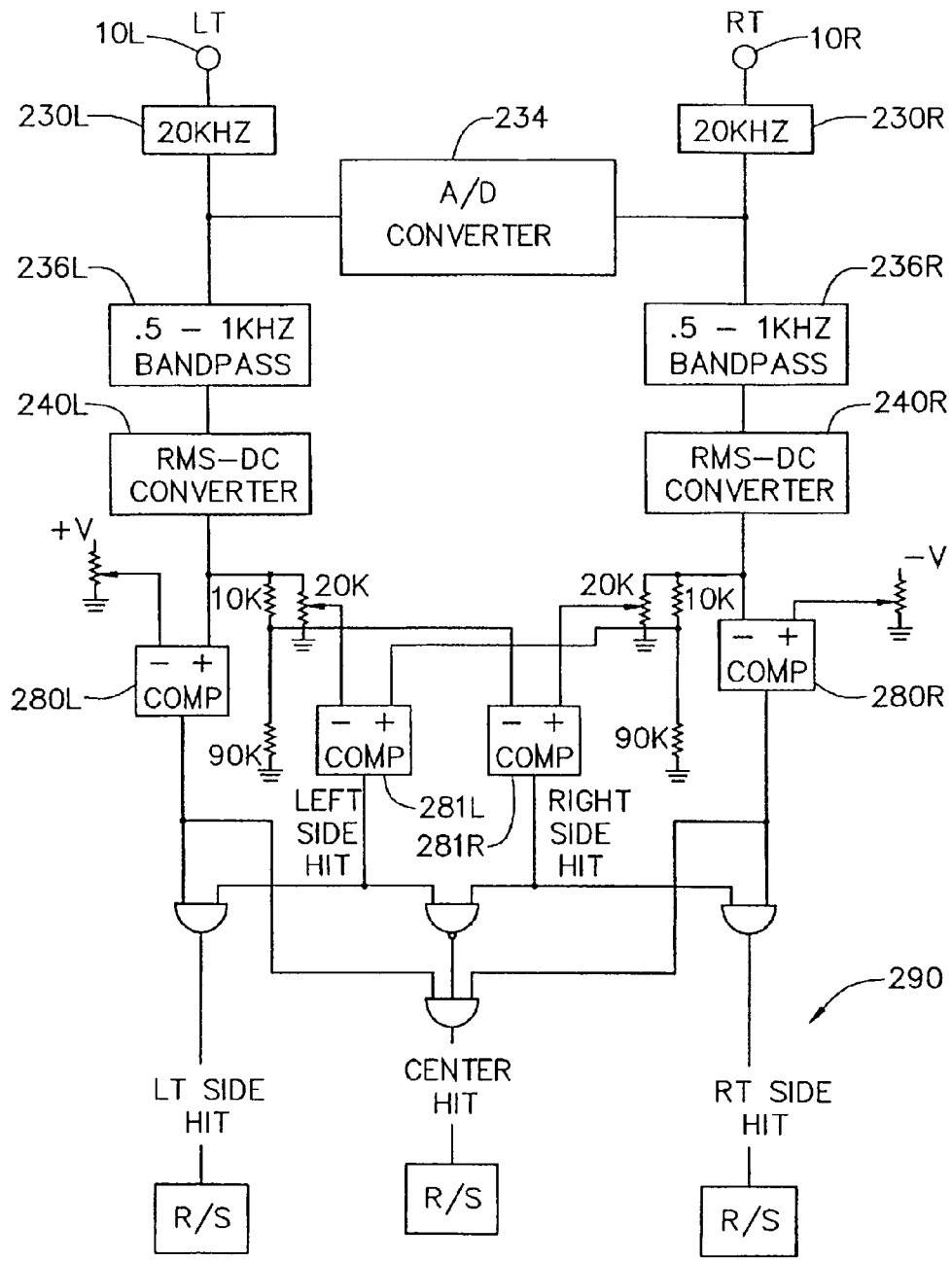
FIG. 6 is a schematic circuit diagram of the impact detection system according to another preferred embodiment of the invention.

Turning now to FIG. 6, there is shown a more detailed diagram of the two channels shown in FIG. 3. However, there are modifications and detailed below. In this case, with reference to the left sensor 10L, the signal is passed to a low pass filter 230L with a 20 kHz cutoff. Likewise, right sensor 10R is connected to a low pass 20 kHz filter 230R. At this point, it should be noted that low pass filters 230L and 230R are not crucial to the invention and need not be present. If provided, both left and right filters 230L and 230R would be input to an analog to digital converter circuit 234 as shown. With reference to the left channel, the signal passes through 500-1000 Hz band pass filter 236L then to a root mean squared DC converter 240L and next to comparators 280L and 281L which checks the signal versus a reference voltage. Finally, a search logic 290 determines whether a hit is a left side hit, a center hit or a right side hit. The right channel has similar circuitry which will not be described separately.

Figure 7:
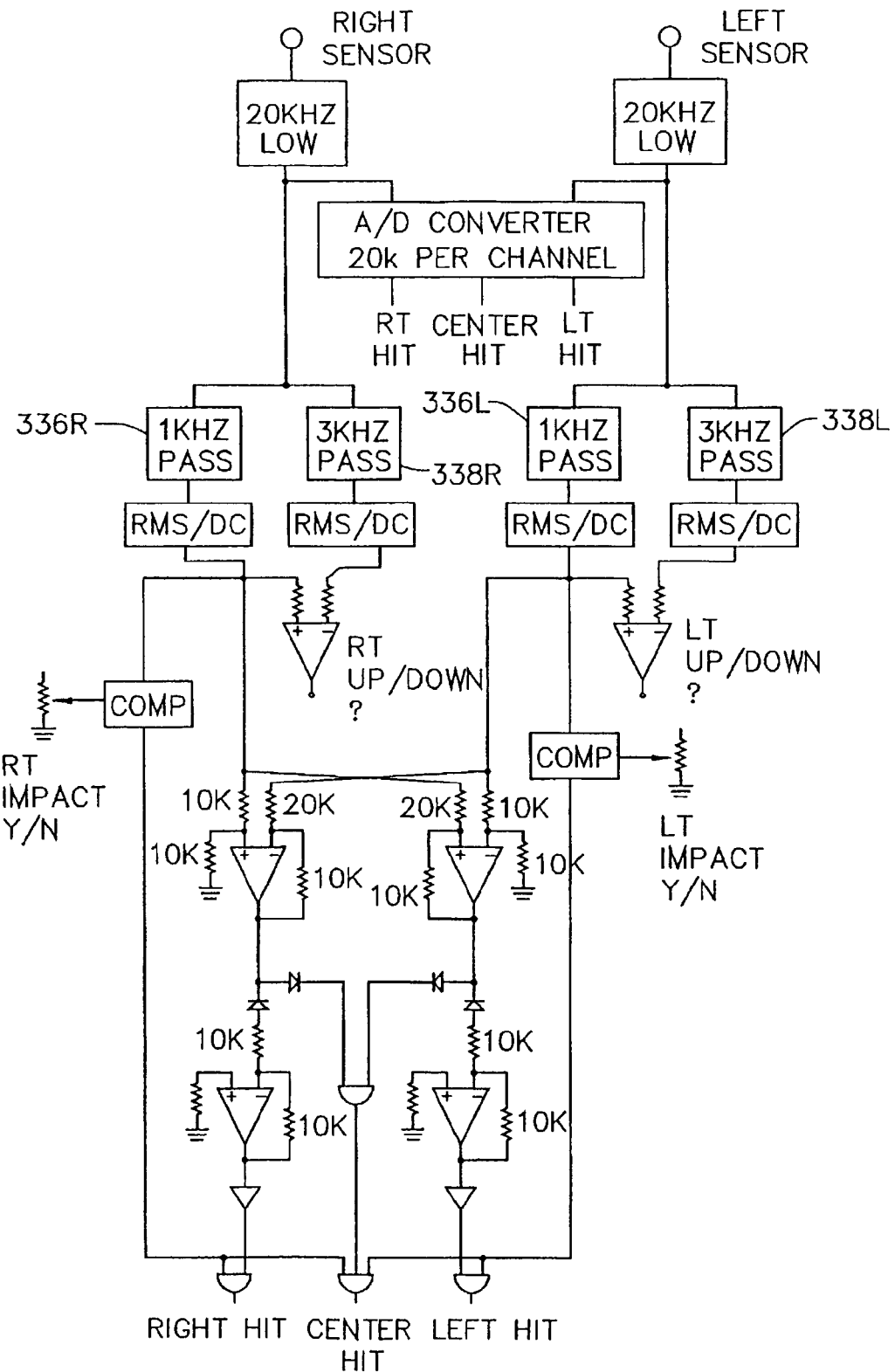
FIG. 7 is a schematic circuit diagram of another preferred embodiment of the impact detection system.

Turning now to FIG. 7, there is shown a more detailed circuit diagram similar to that shown in FIG. 6. However, this diagram includes both 1 kHz and 3 kHz band pass filters 336L, 336R, 338L, 338R for each channel. These filters pass 500-100 Hz for the kHz filters 336L and 336R and pass 2000-4000 Hz for the 3 Hz filters 338L and 338R. The relative strength of the signal from each type of filter provides additional information regarding the impact.

Turning now to FIGS. 8A-8C, there is shown again left and right channels coming from left and right sensors 10L and 10R. The channels correspond to those shown in FIG. 6. In this case, the low pass filters 230L and 230R (again optionally shown) are specified as UAF 42 microchips and their pin configurations are shown with each pin connected to an appropriate electrical element to set each filter at the 20 kHz level. Next, in each channel is shown another UAF 42 microchip, this time set to be a respective band pass filter 236L, 236R. Again, low pass filter 230L and 230R are optionally shown. If not provided, the output from a respective sensor 10L, 10R would be sent to pin 2 of a respective band pass filter 236L, 236R as represented by the dotted lines in FIG. 8A. Next shown in each channel are AD 637 microchips which act as rectifiers 240L and 240R of the block diagram shown in FIG. 6. Furthermore, the pin configuration of four different comparators 280L, 281L, 280R and 281R are shown in FIG. 8B. These comparators 290 are equivalent to those shown in FIG. 6. Finally, the details of the logic gates shown in FIG. 6 are shown in much more detail in FIG. 8C.

Figure 8A:
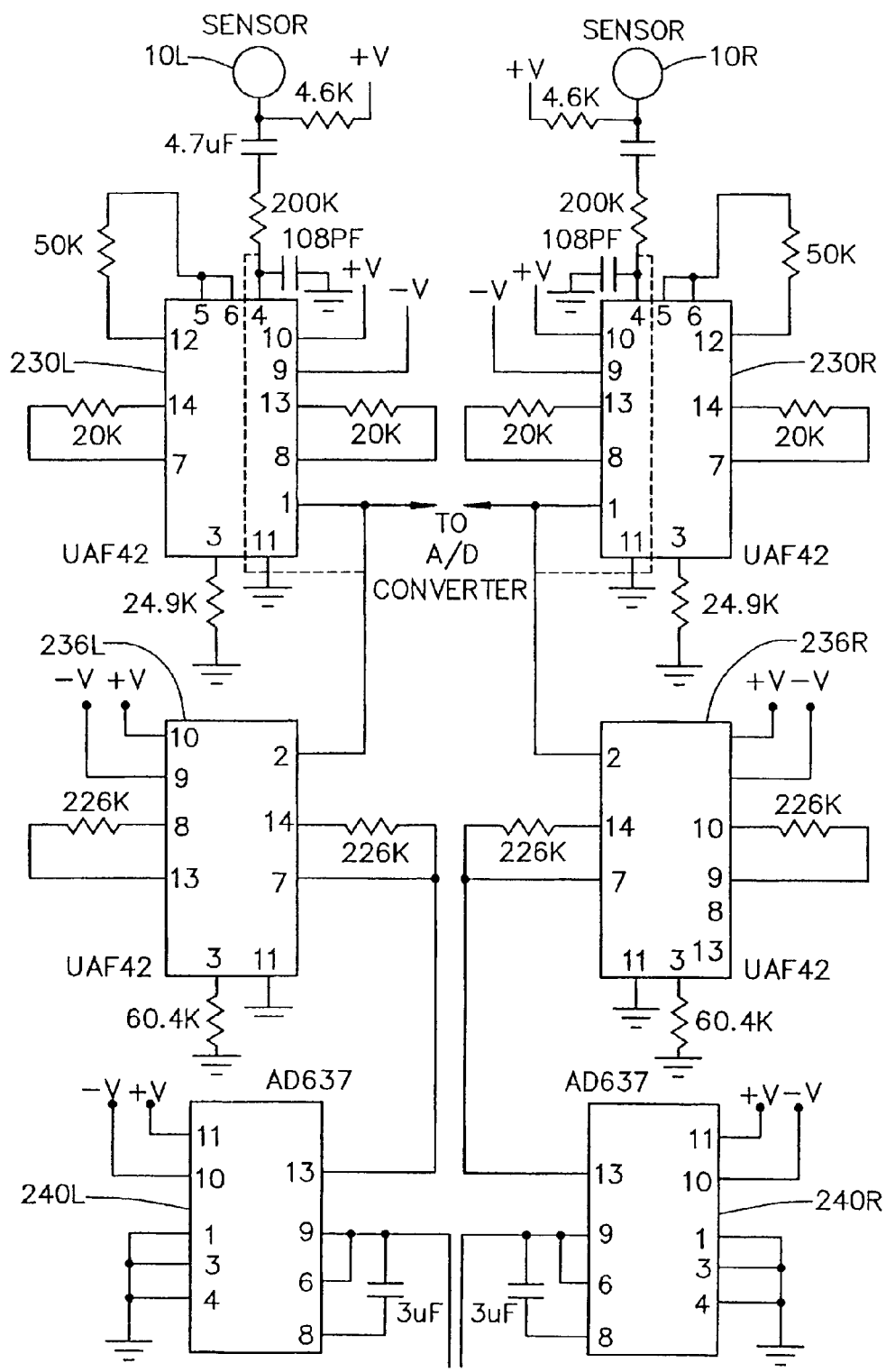
FIGS. 8A-8C are circuit diagrams of the impact detection system.
Figure 8B:
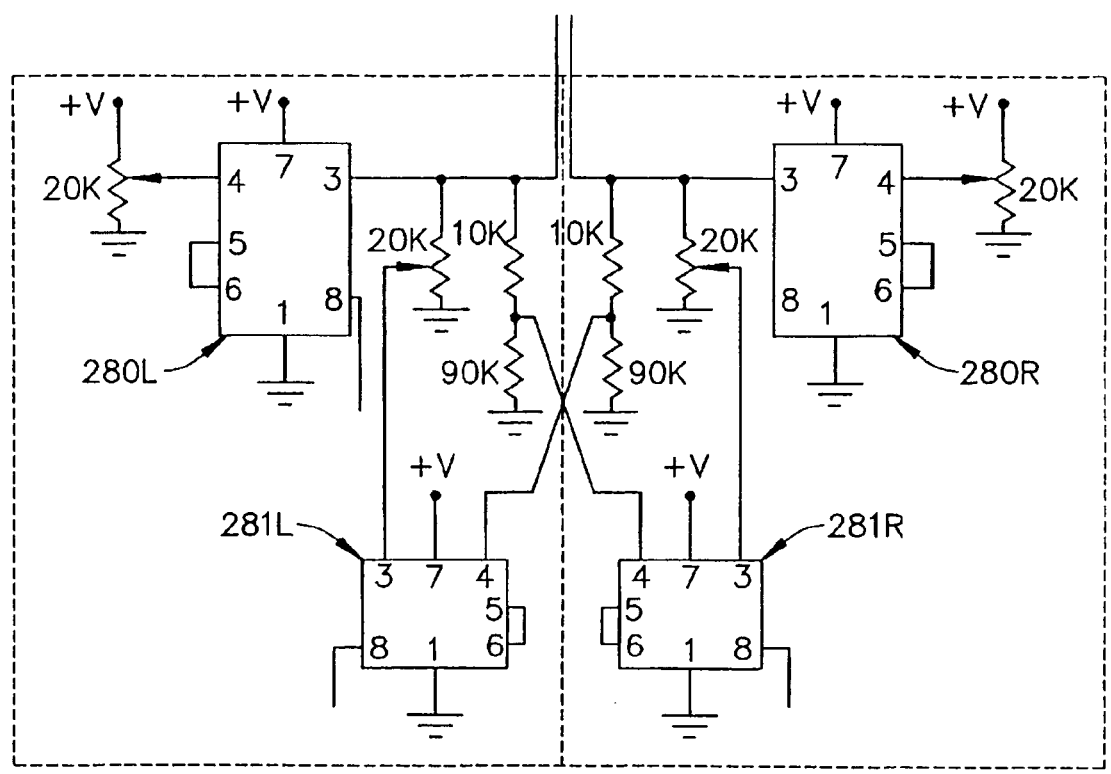
Figure 8C:
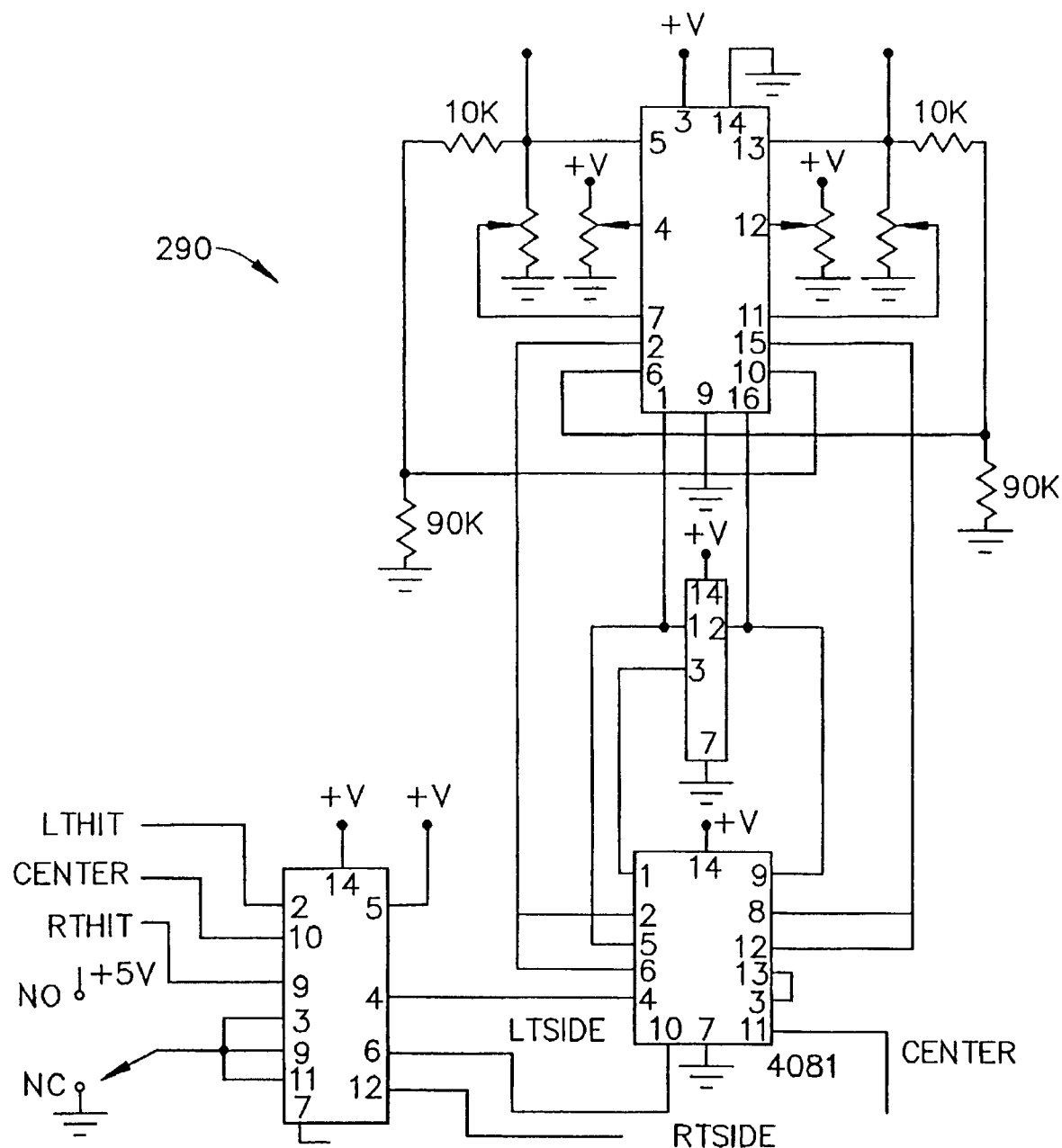
Figure 9:
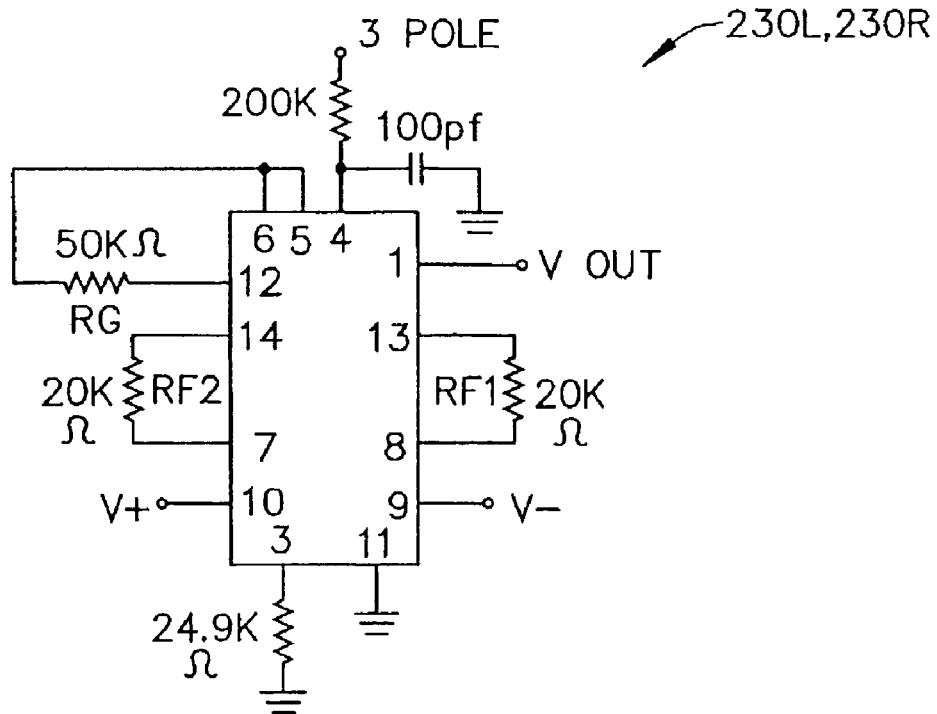
FIG. 9 is an enlarged diagrammatic view of the low pass filter of FIG. 8A.
Figure 10:
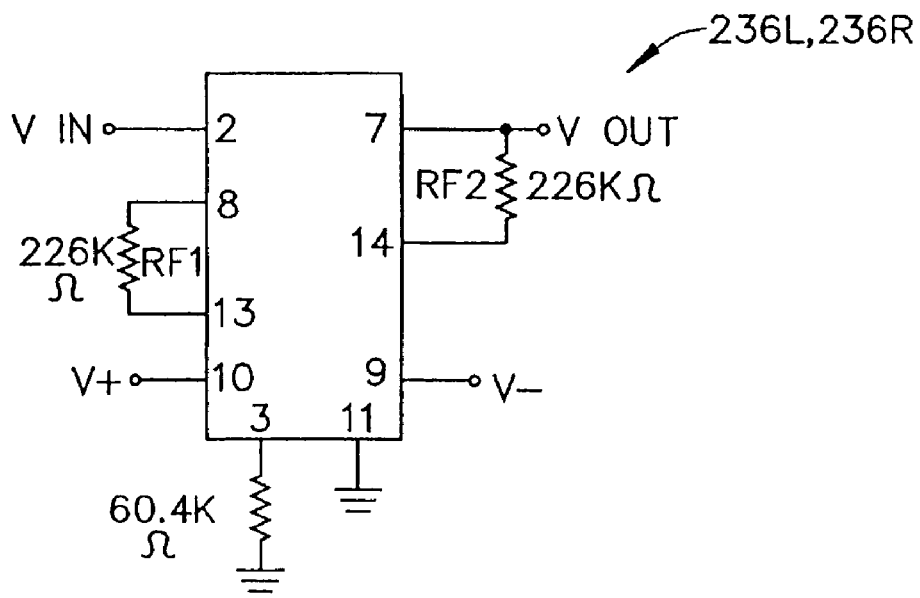
FIG. 10 is an enlarged diagrammatic view of the band pass filter of FIG. 8A.

FIG. 9 is simply a close-up of a UAF 42 chip shown in a low pass filter mode set at 20 kHz and is a more detailed view of one of the UAF 45 chips 230L, 230R shown in FIG. 8A. Again, it should be noted that low pass filters 230L and 230R are optional as discussed above with particular reference to FIG. 8A. Likewise, FIG. 10 shows another UAF 45 chip 236, this time set up to be one of the band pass filters 236L or 236R as shown in FIG. 8A.

Figure 11:
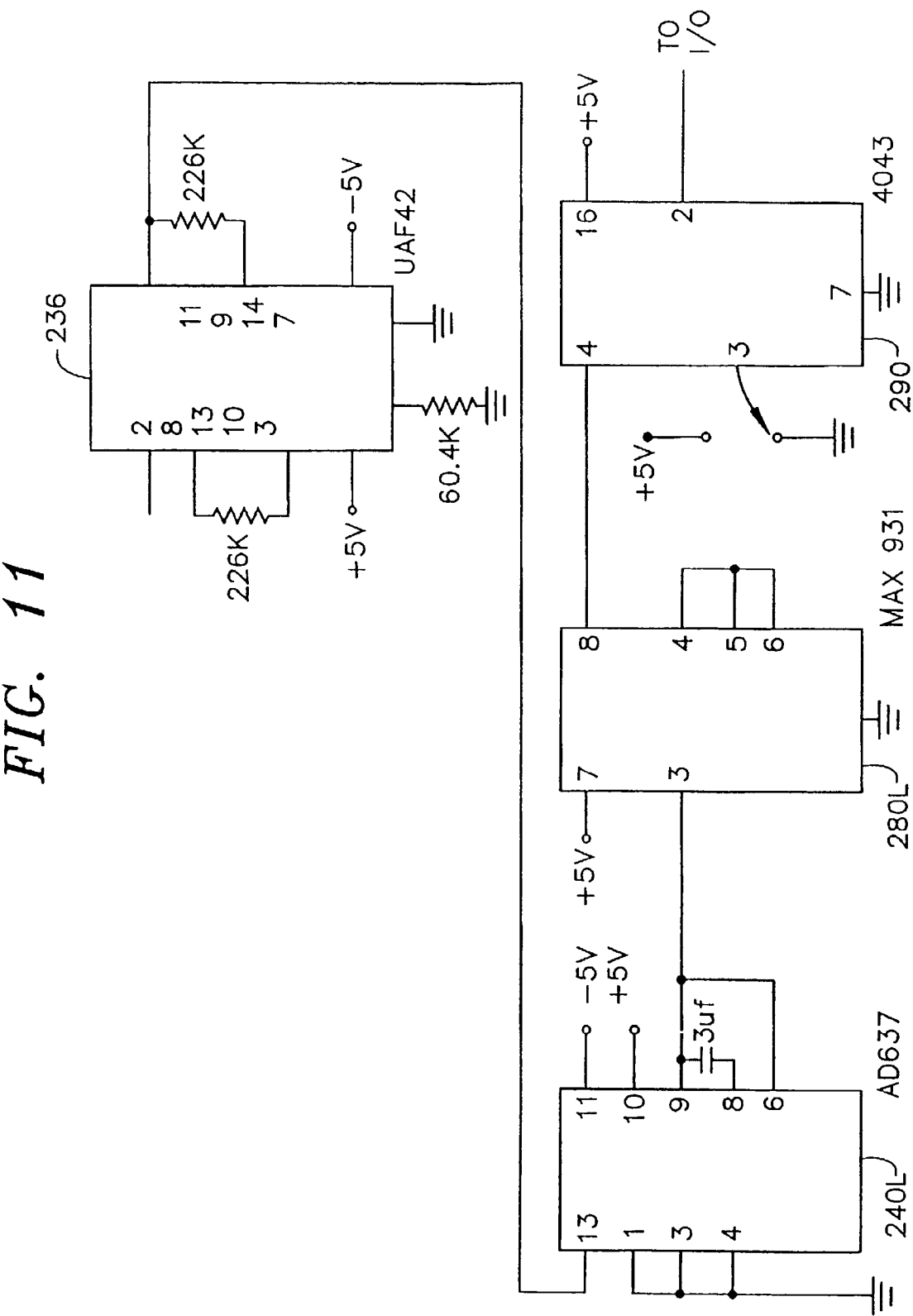
FIG. 11 shows one channel of the embodiment shown in FIGS. 8A-8C.
Figure 12A:
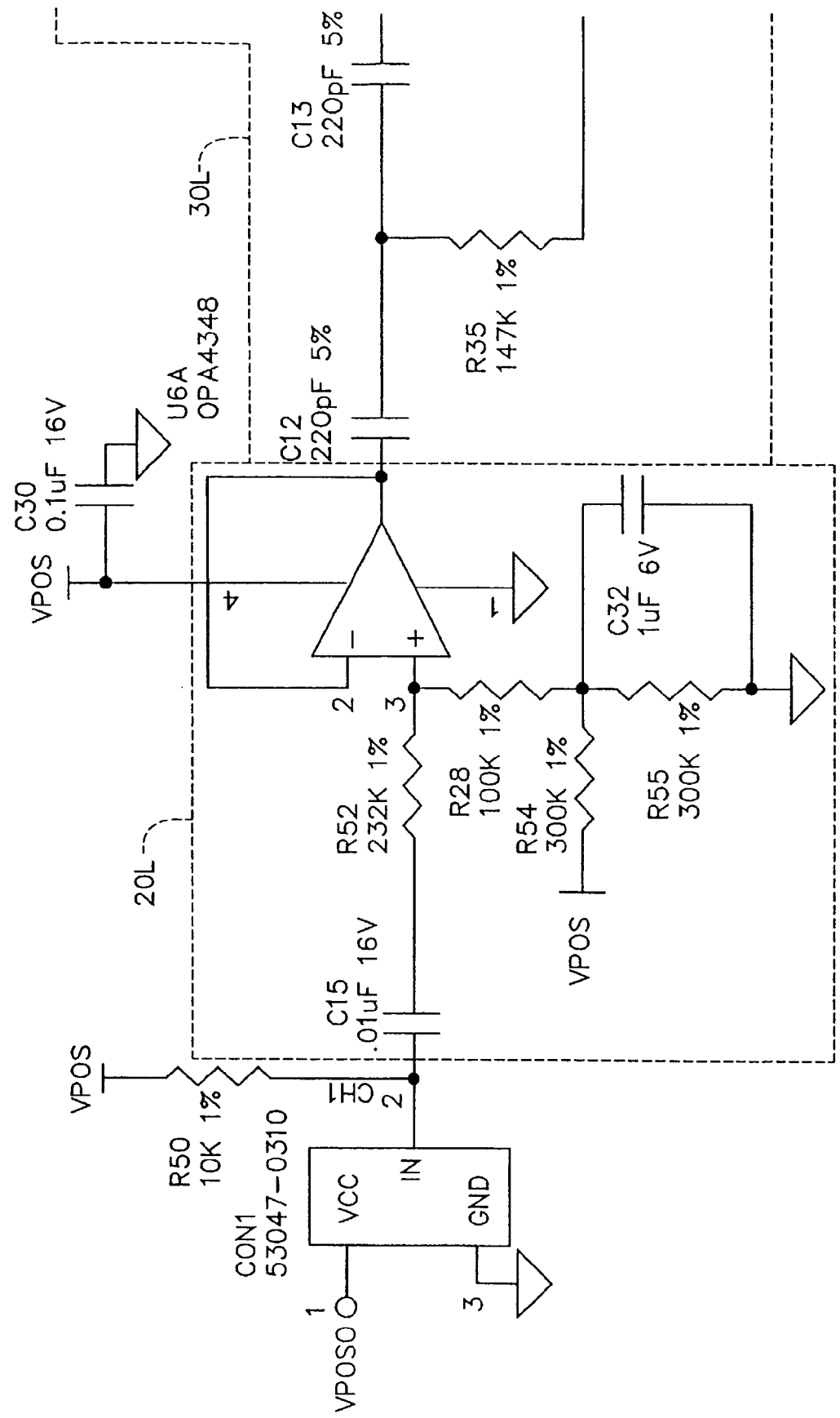
FIGS. 12A-12H, 13A-13D and 14 show a more detailed circuit diagram of the ballistic impact detection system of FIG. 3.
Figure 12B:
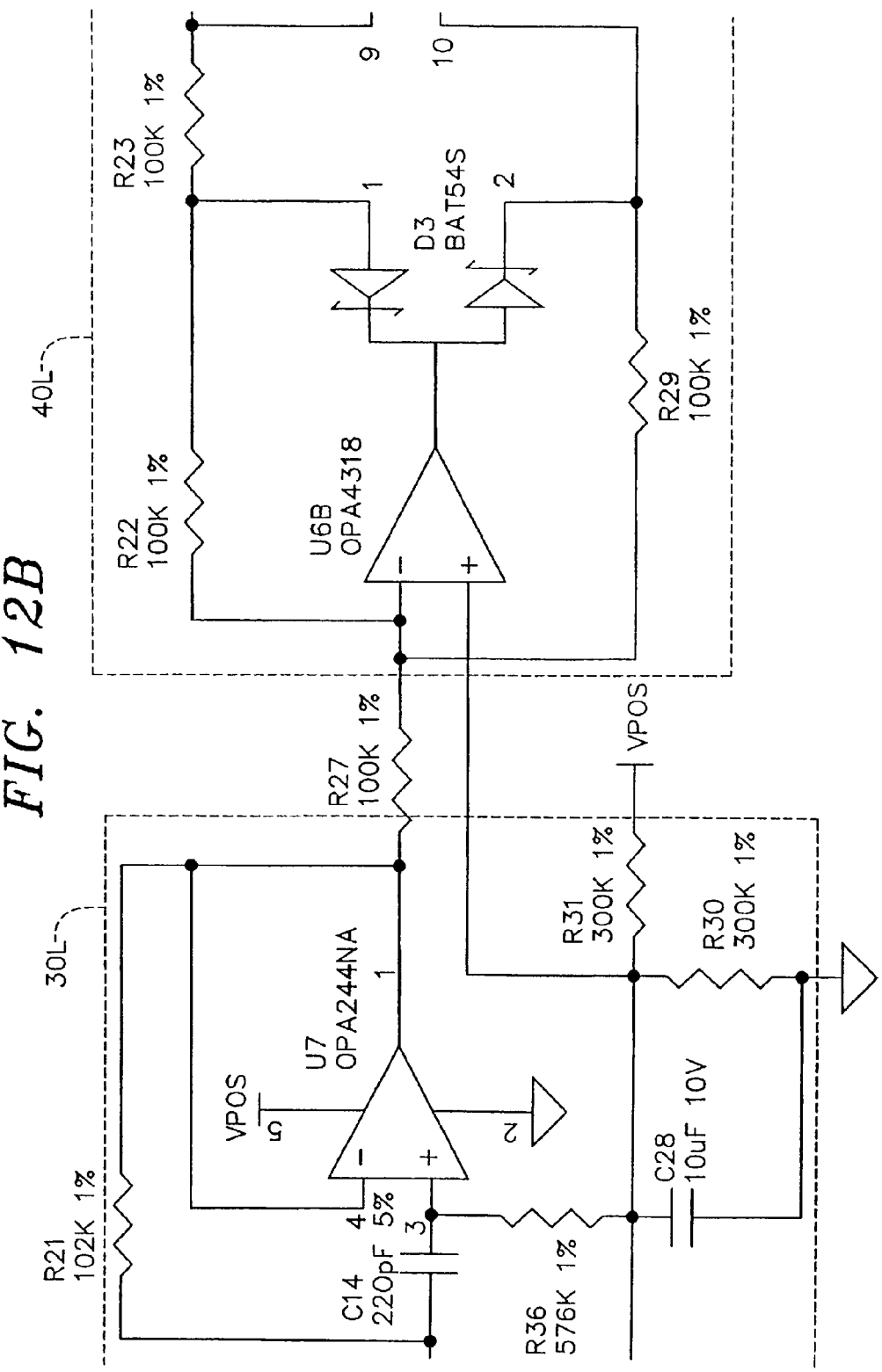
Figure 12C:
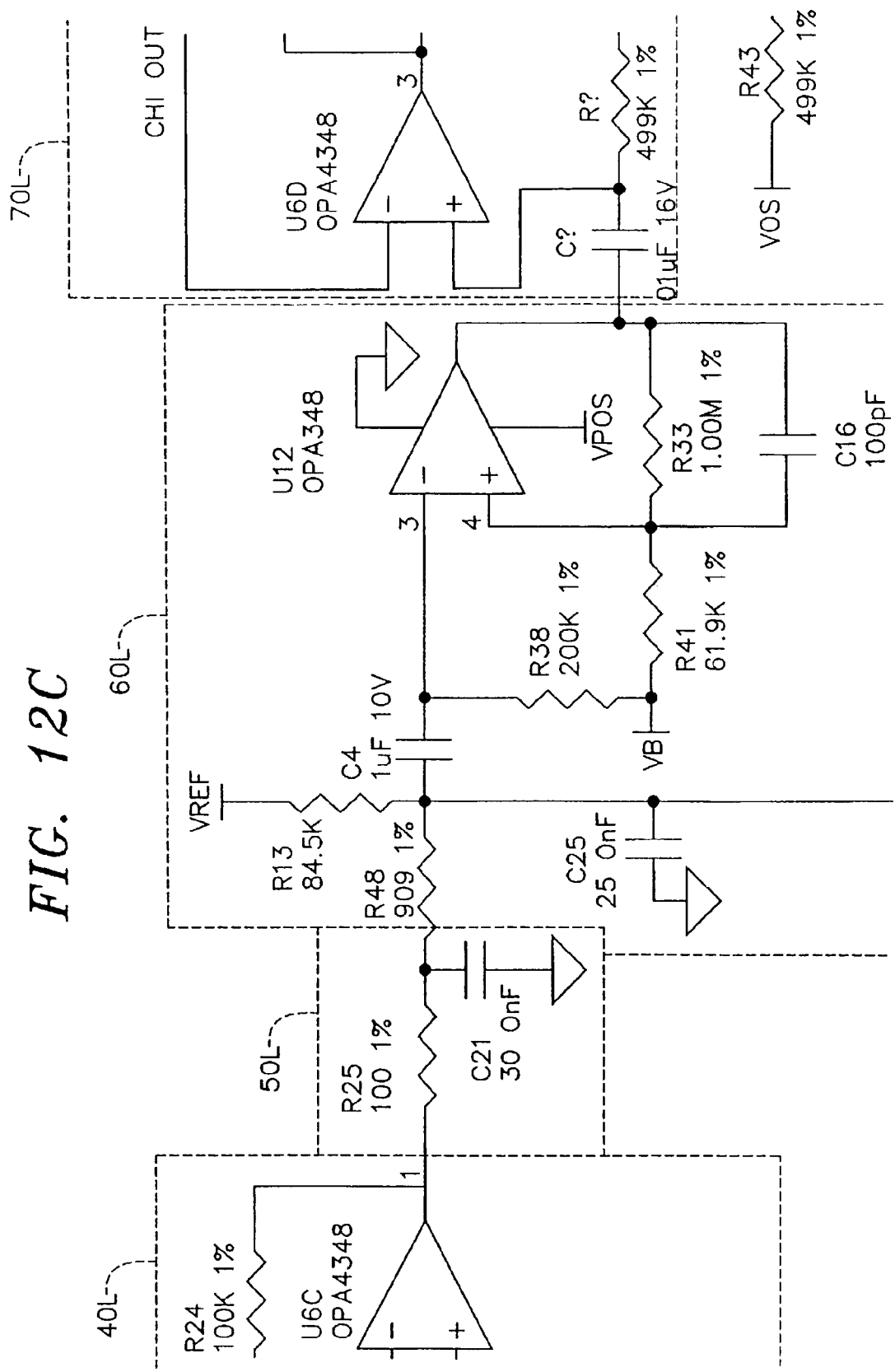
Figure 12D:
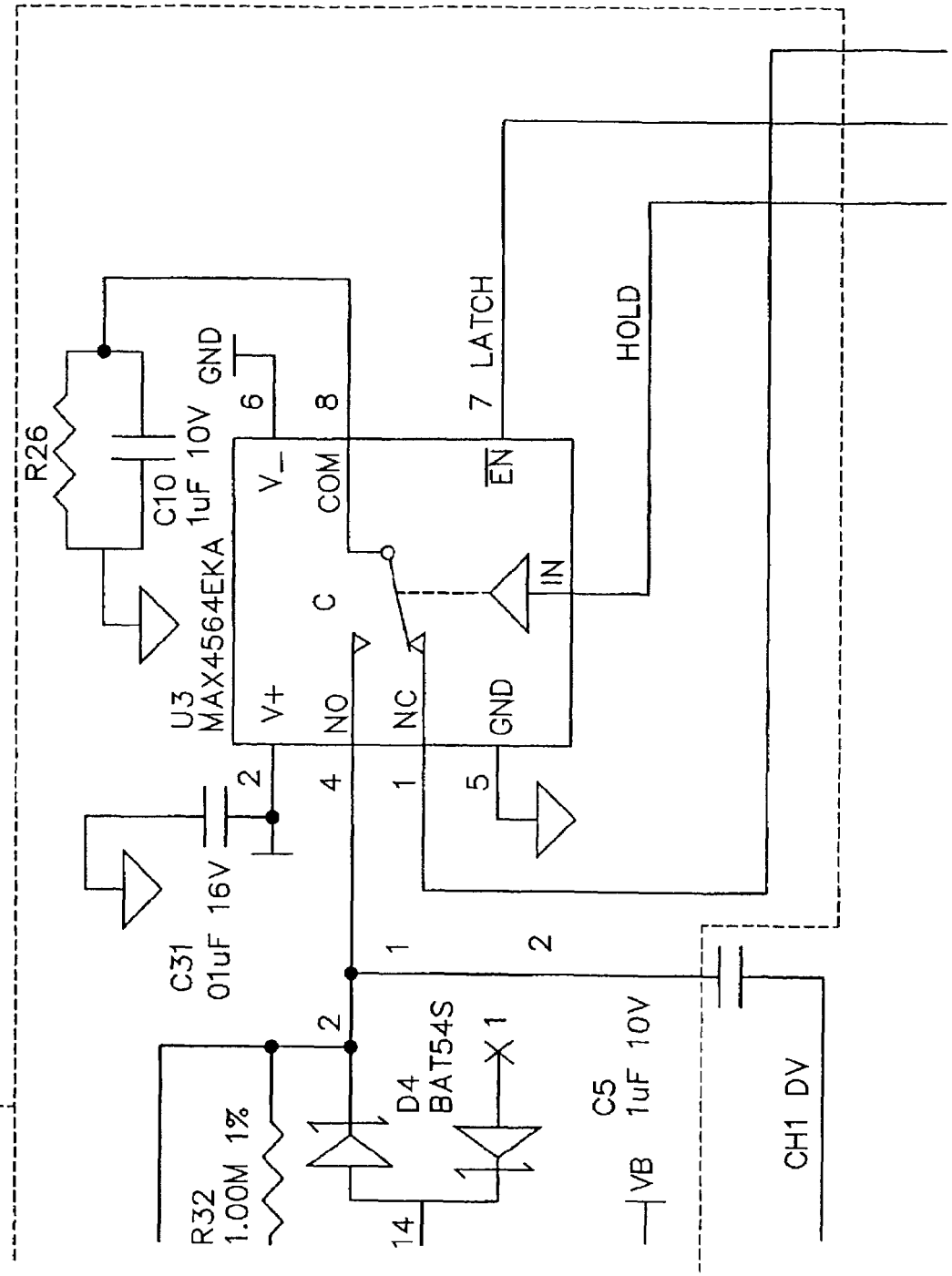
Figure 12E:
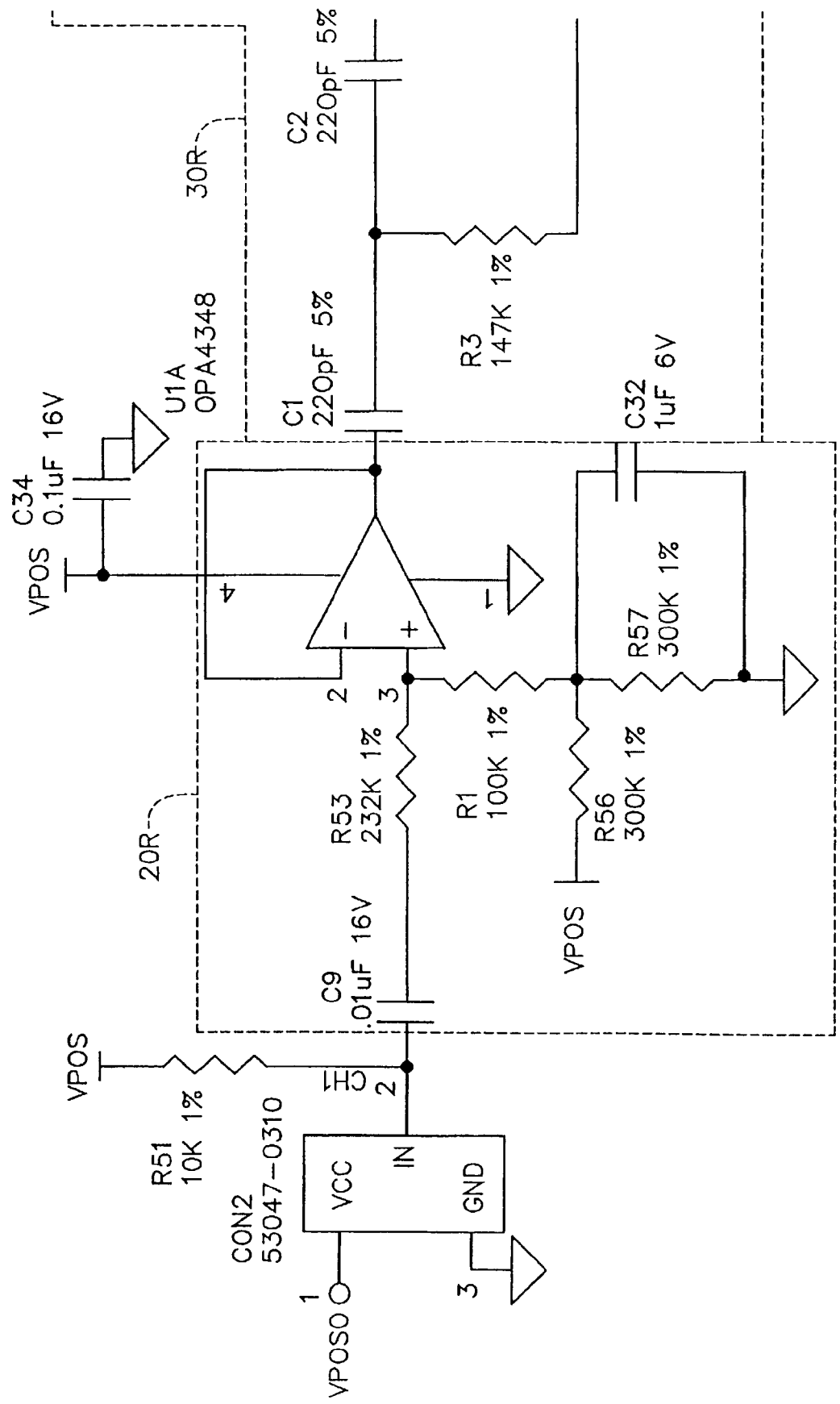
Figure 12F:
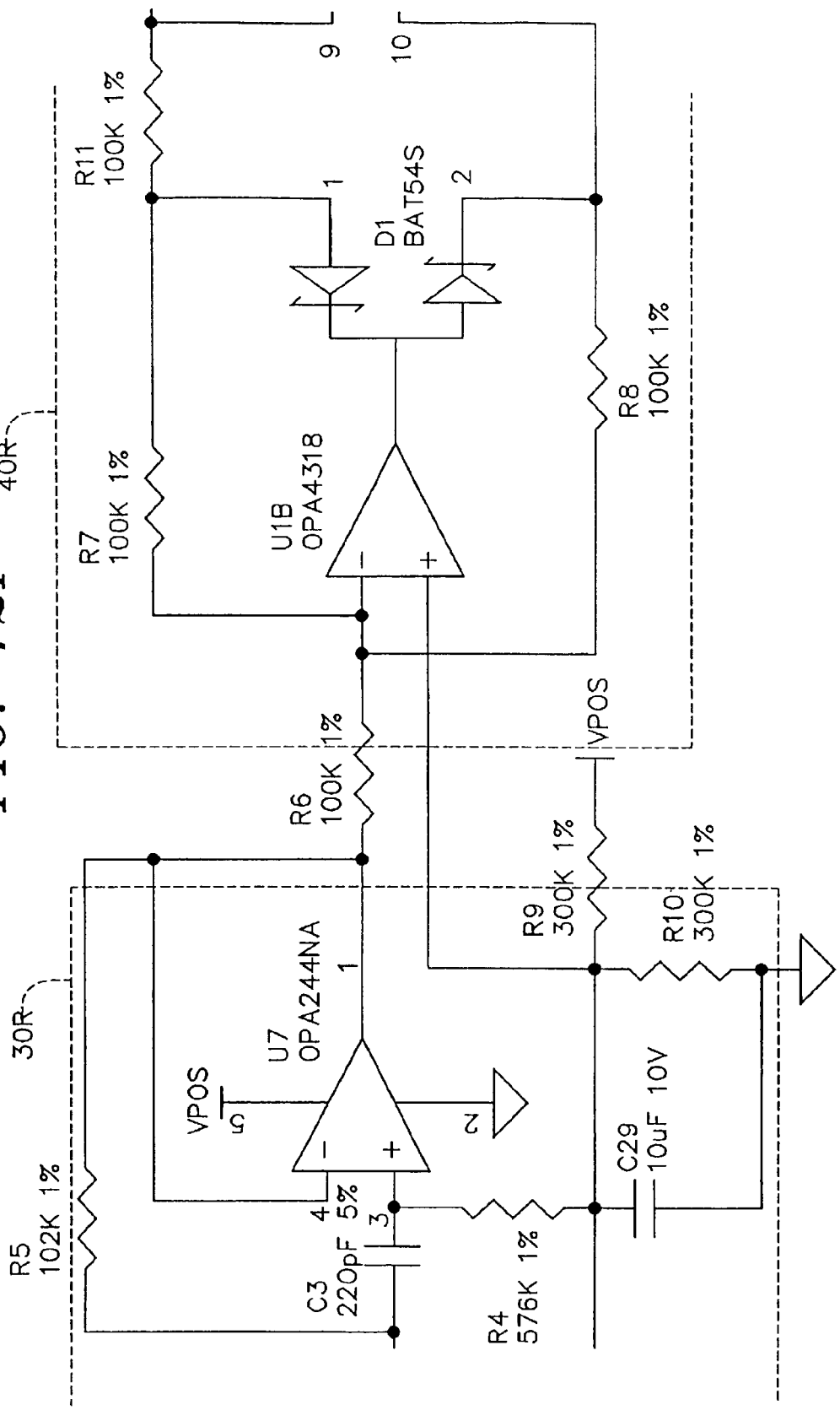
Figure 12G:
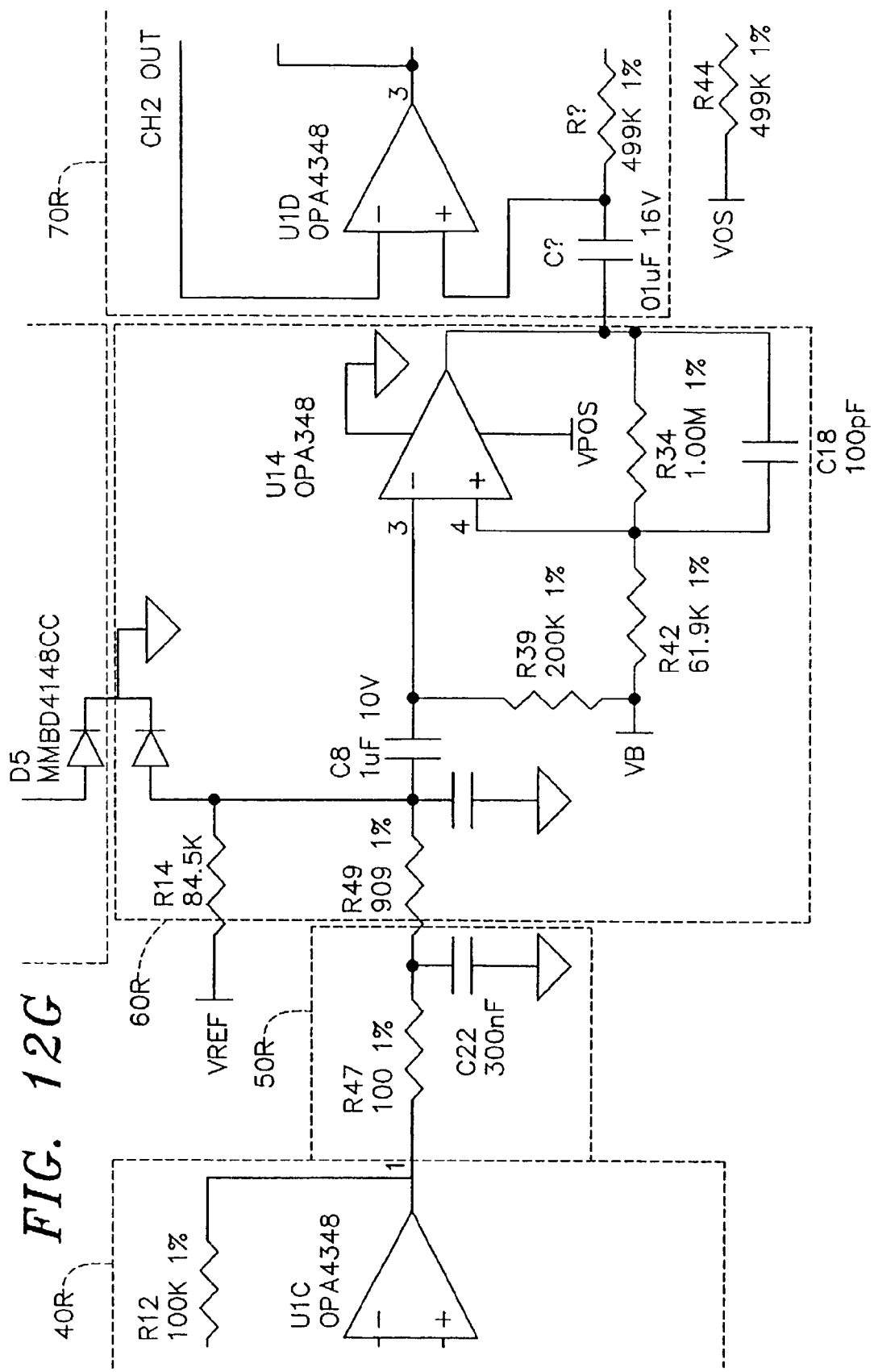
Figure 12H:
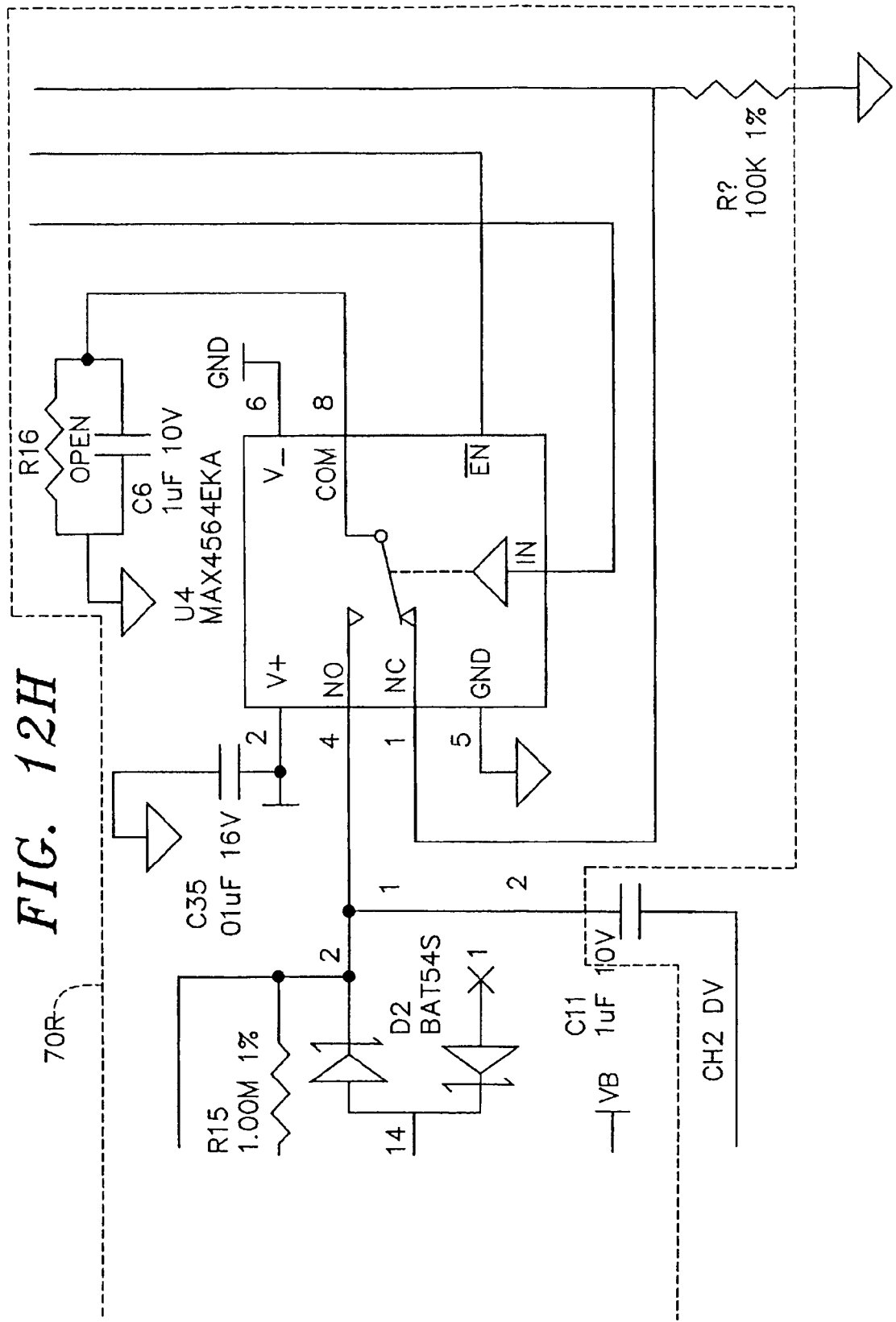
Figure 13A:
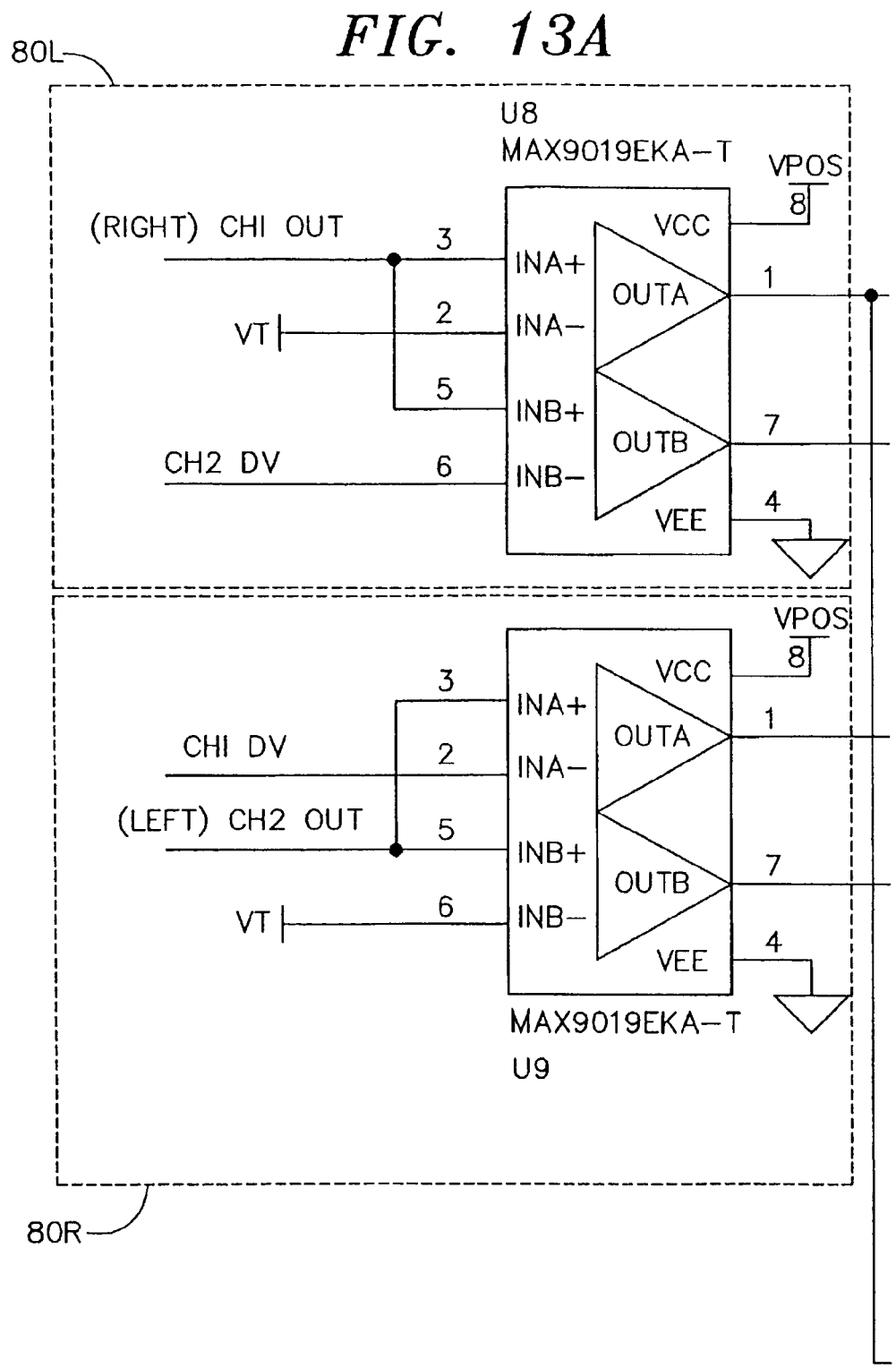
Figure 13B:
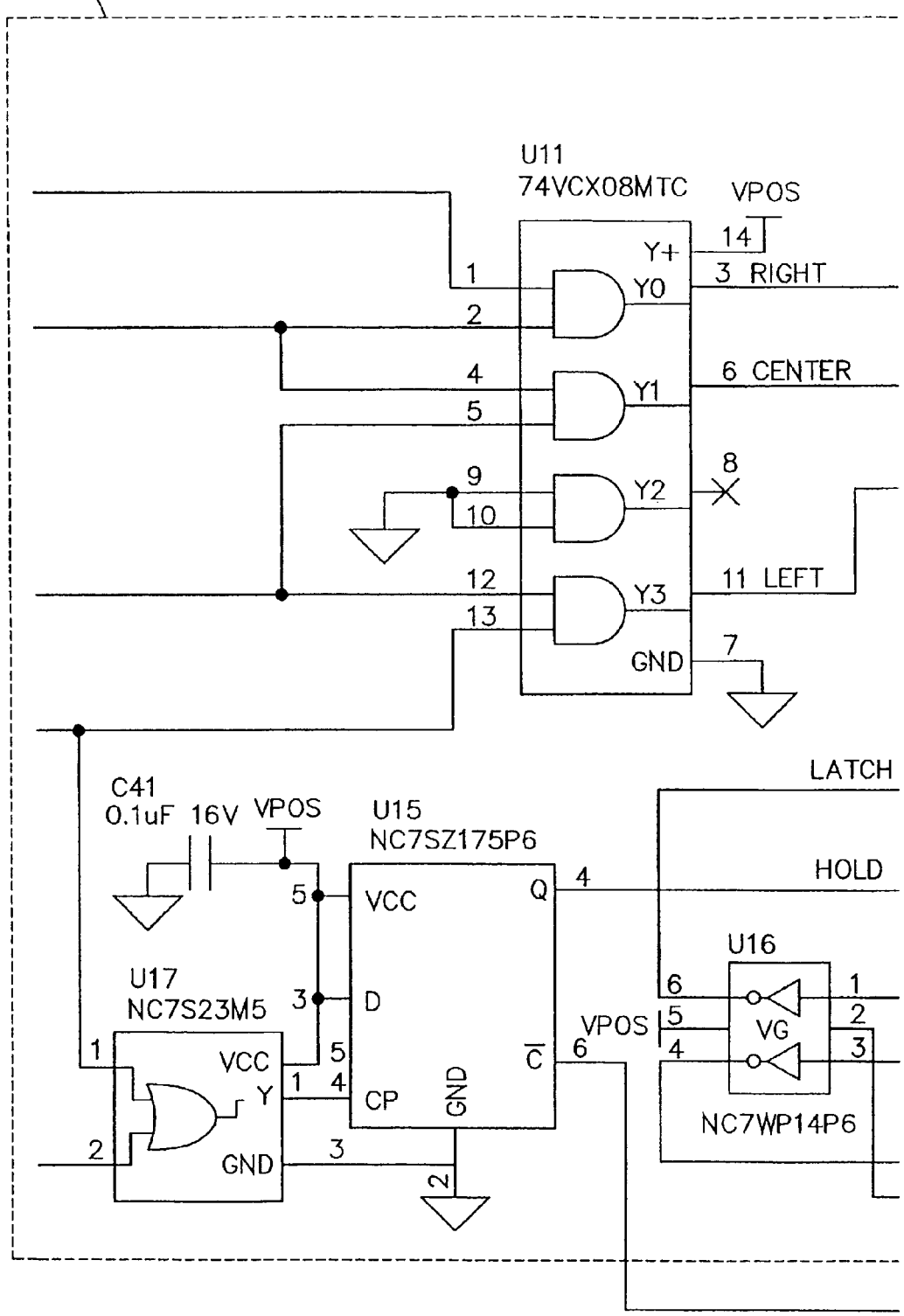
Figure 13C:
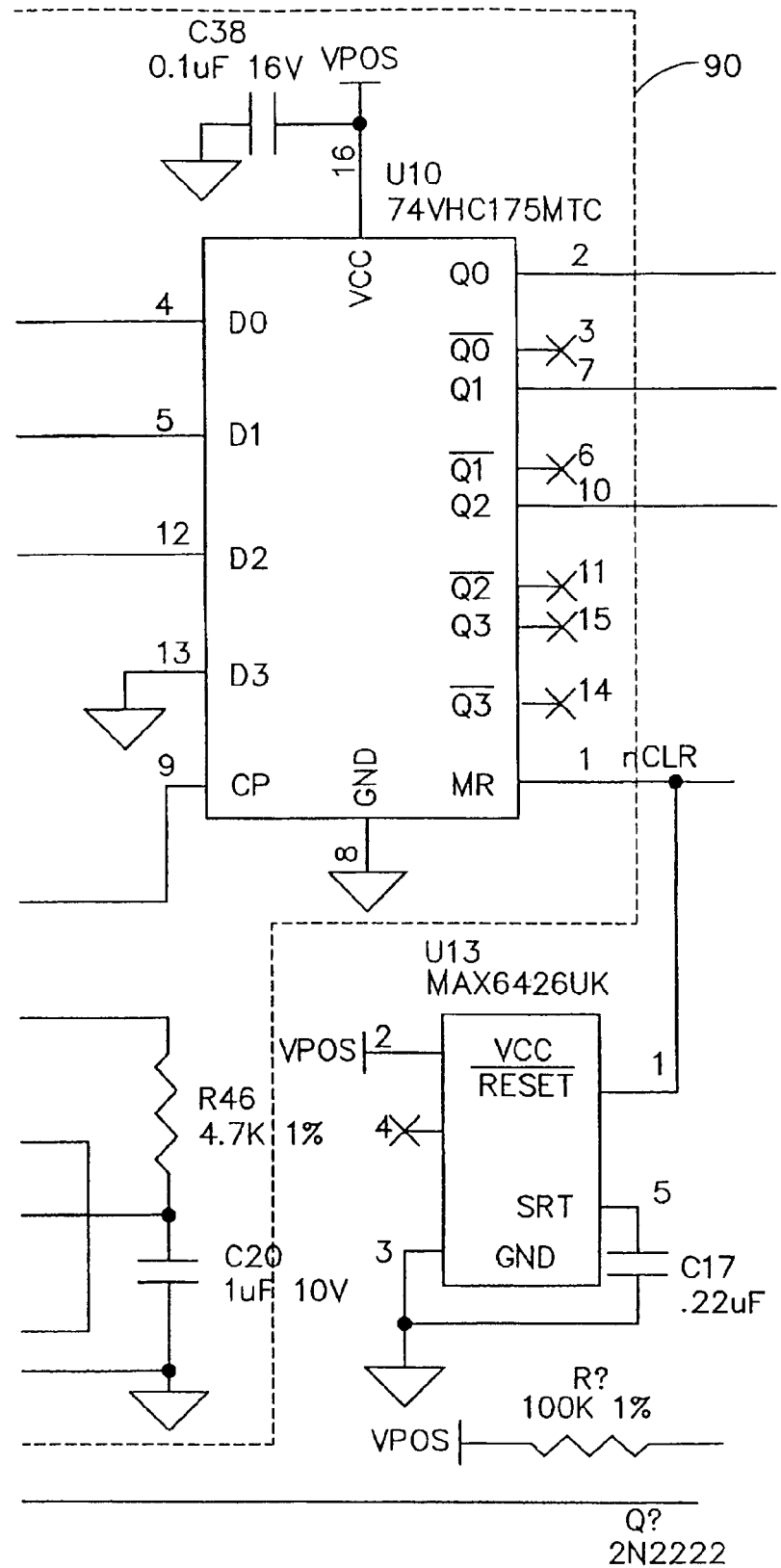
Figure 13D:
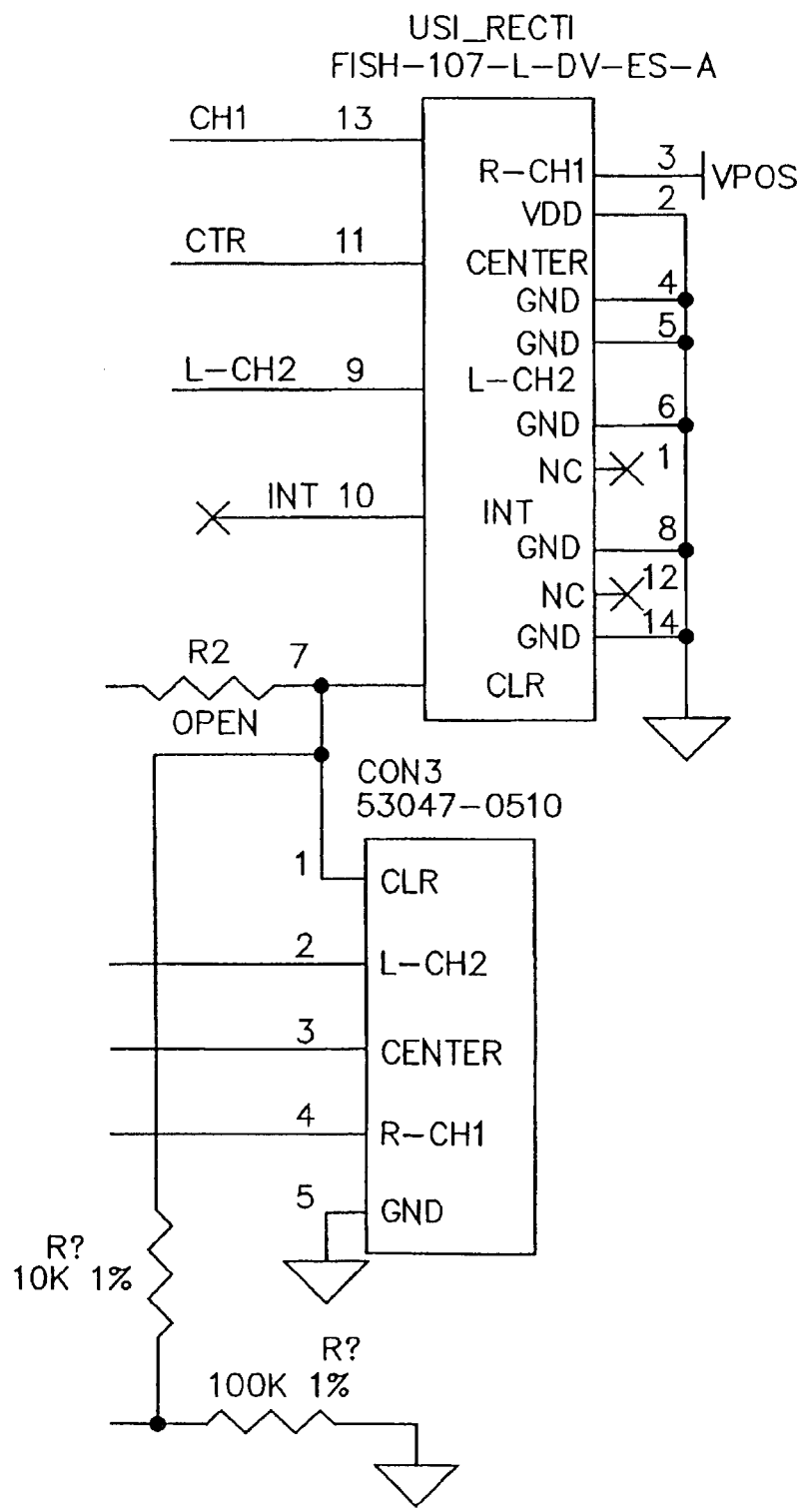

FIG. 11 shows a single channel of the embodiment shown in FIGS. 8A and 8B. First shown is the UAF microchip 236 set to act as a band pass filter. Next shown is the AD 637 microchip 240 which is acting as a rectifier. Next is shown a comparator 280 labeled MAX 931, which is one of the comparators shown in FIG. 8B. Finally, a 4043 microchip 290 is shown which sends a signal on for further processing.

Figure 14:
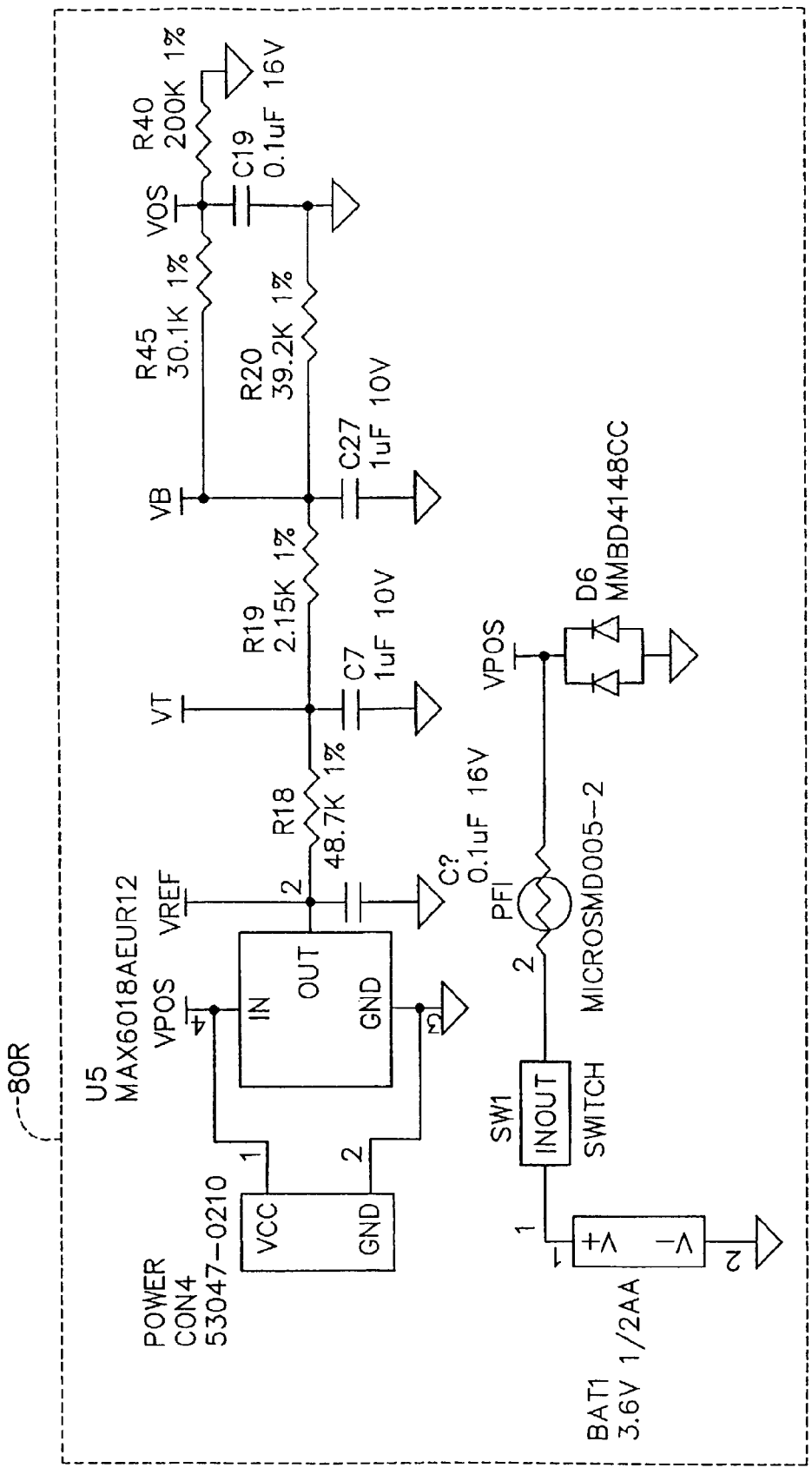

Although considered to be shown in sufficient detail in reference to the figures discussed above, for the sake of completeness a further detailing of preferred circuitry will be briefly discussed with reference to FIGS. 12A-13D and certain test results below. However, at this point, is should be understood that the particular circuitry employed could take various forms, while still achieving the desired results. FIGS. 12A-12H show the left channel of the BIDS circuit represented in FIG. 3. Note, once again, sensor 10L is connected to an input amplifier 20L which then sends a signal to high pass filter 30L, which, in turn, sends a signal to full wave rectifier 40L. Next in the sequence is low pass filter 50L which connects to logarithmic unit 60L and next to peak hold circuit 70L. Likewise, FIGS. 12E-12H show the right hand channel of the BIDS circuit represented from FIG. 3. Sensor 10R is connected to input amp 20L which then sends a signal to high pass filter 30R, which in turn, sends a signal to full wave rectifier 40R. Next in the sequence is low pass filter 50R which connects to logarithmic unit 60R and next to peak hold circuit 70R. FIGS. 13A-13D show the end of the channel 5 shown beginning with 13A showing left and right threshold circuits 80L and 80R, while 13B-13D show the logic circuitry 90. Finally, FIG. 14 presents a detailed view of the preferred circuitry for threshold circuit 80R.

Regardless of the particular circuitry employed, the current two sensor embodiment, if the amplitude signals from sensors 10L and 10R are less than a 2:1 ratio and at least one sensor signal meets the threshold voltage requirement, the impact is deemed to have occurred between the sensors or in a center location. If the ratio of the signals is greater than 2:1 and the greater signal also meets the threshold voltage requirement, the location is deemed to be distal to the sensor with the greater amplitude signal. Thus, in the two sensor embodiment, three locations are possible: center; right and left. The voltage signals for these location outputs are latched and then available to be read or transmitted to a computer. Once read, the BIDS accepts a reset voltage signal which returns the location outputs to ground. In its current embodiment, the BIDS circuitry can distinguish one impact in each location until a reset is received. The current analog BIDS circuit measures 1.5 square inches and requires approximately 600 microamperes of current at 3 volts.

A further aspect of BIDS is linking the impact detection with the wounding severity to provide the medic with as much triage information as possible. At this point, it should be noted that the BIDS can be based on a digital signal processor which would sample the incoming analog voltage from the sensors, establish Fast Fourier Transforms and perform power analysis on the signals to determine impacts and locations. Sophisticated algorithms could be established to tell from frequency analysis whether a bone has been struck and from power analysis whether an exit wound exists. In this digital embodiment, BIDS would track multiple impacts in the same general location, as well as potentially providing an indication of wounding severity.

Figure 16A:
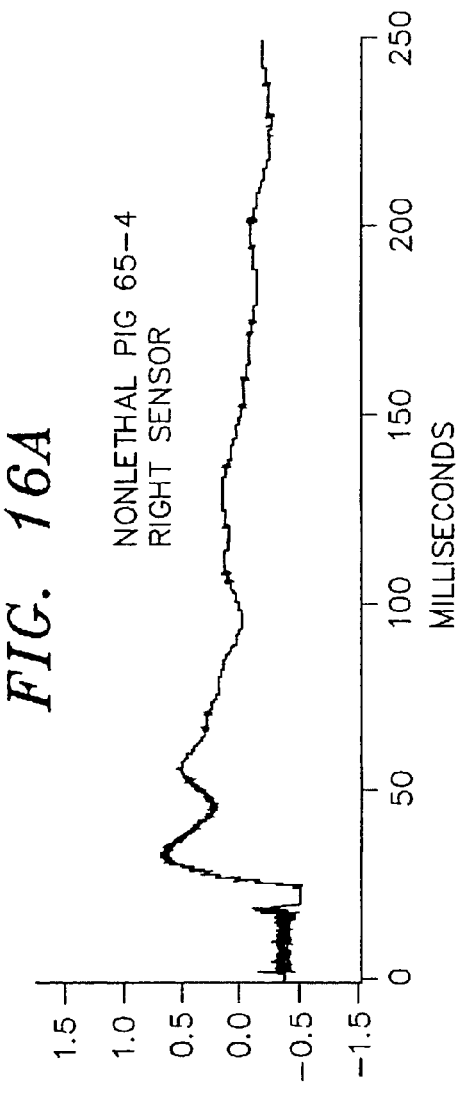
FIGS. 16a and 16b show a shock wave amplitude of a left sensor being greater than the amplitude of a right sensor confirming that an impact site was in the left lateral chest.
Figure 16B:
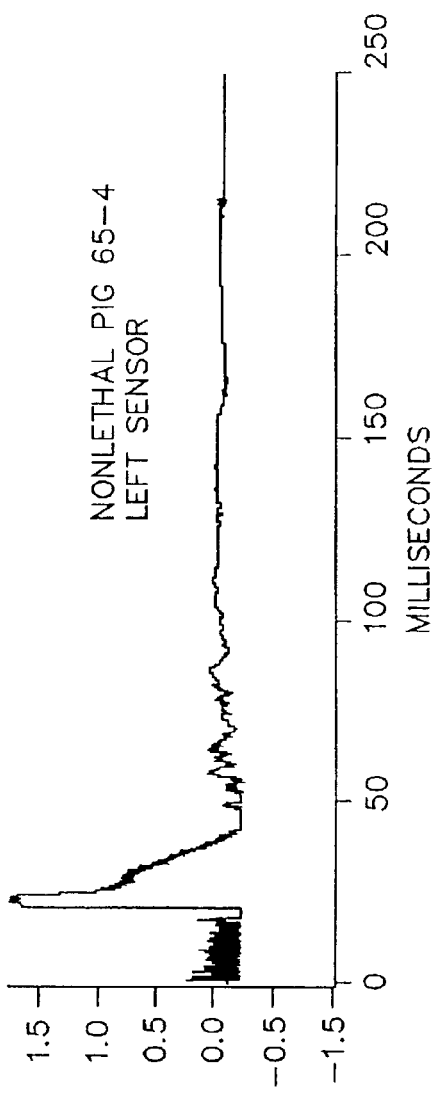
Figure 15:
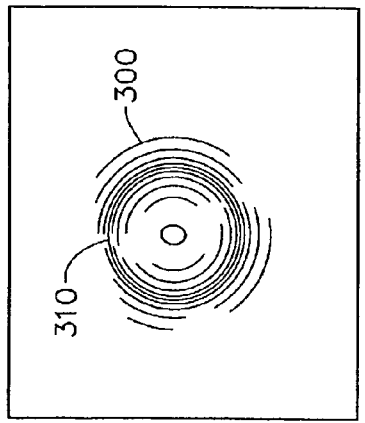
FIG. 15 shows an impact of a left lateral chest area.

In connection with the creation and testing of the Ballistic Impact Detection System (BIDS) of the invention, hypothesis outlined that acoustic vibrations on the skin created by penetrating ballistic missiles could be sensed and analyzed to determine severity of the wounding event. A proof-of-concept phase was conducted with the acquisition of impact signatures from a swine model used in a non-lethal wounding protocol. During this protocol, a single 'plastic bullet' (a 12 mm steel bearing ball with a thin plastic coating weighing approximately 16 grams) was fired from a gas gun at an anesthetized pig (referenced as Test ID 65-4) from a distance of 8 feet. Three impact locations were used—lateral chest, sternum, and abdomen. Velocities ranged from 239 to 298 feet/second. Two Piezo-film sensor elements were attached using duct tape to the back of the animal, symmetrically about the spine just below the scapulas or symmetrically about the sternum. The voltage response from the sensor elements were digitized at 20,000 samples per second and digitally recorded. FIG. 15 illustrates an impact to the left lateral chest for one test (Test ID 65-4). Analysis of the impact signatures showed consistent characteristics. Each waveform was made up of two distinct frequency patterns. The first pattern was a low-amplitude, high-frequency section lasting on the order of 20 milliseconds. The second pattern was a high-amplitude, low-frequency section. FIGS. 16A and 16B show exemplary voltage recordings.

Figure 17:
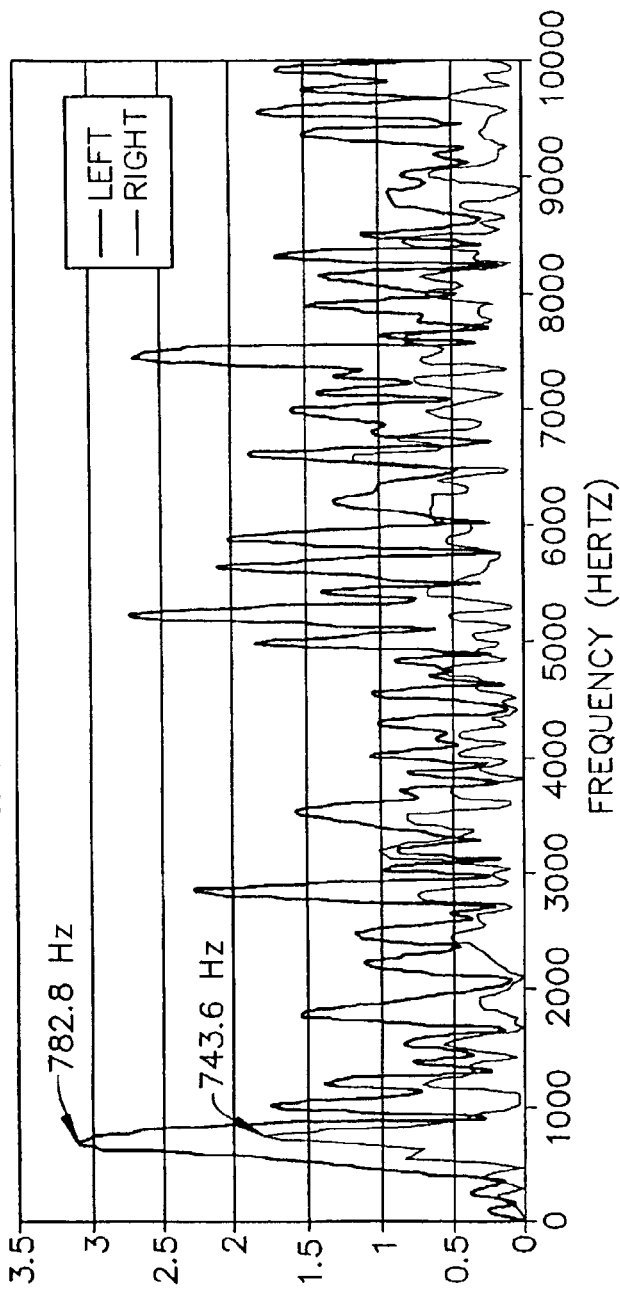
FIG. 17 shows the Fast Fourier Transform performed on an initial 7.5 milliseconds of a shock wave of an impact.

For purposes of this disclosure, we will refer to the high frequency section as the shock wave and the lower frequency section as the tissue displacement wave. FIG. 15 shows the two frequency sections, the shock wave as a fast moving slight rippling 300 effect that moves outward from the impact site and the slower developing tissue displacement wave 310 radiating outward tantamount to ripples in a pool. Examination of FIGS. 16A and 16B show that the shock wave amplitude of the left sensor 10L is greater than the amplitude of the right sensor 10R, confirming that the impact site was the left lateral chest. Examination of the tissue displacement waves also confirms a left side hit. They also show that, once formed, they move rapidly as witnessed by the imperceptible delay of the tissue displacement waves between the sensors. Frequency analysis in the form of Fast Fourier Transforms (FFT) was performed on the waveforms. FIG. 17 shows the FFT performed on the initial 7.5 milliseconds of the shock wave for Test ID 65-4. Peak frequencies in the range from 500 to 1000 Hertz were typical in all shots. The peak frequencies (frequencies with the highest power) in this range from this analysis are tabulated in Table 2. FFTs were also performed on the tissue displacement section of the waveform. In every case the predominant frequency of the tissue displacement wave was 98 Hz±19 Hz.

TABLE 2

| Test ID | Primary Right Frequency | Primary Left Frequency | Impact Area |
|---|---|---|---|
| 11-5 | 645.8 | 508.8 | Stomach |
| 12-11 | 763.2 | 547.9 | Chest |
| 12-9 | 665.4 | 743.6 | Stomach |
| 13-11 | 684.9 | 665.4 | Chest |
| 22-9 | 724.1 | 489.2 | Abdomen |
| 24-10 | 547.9 | 782.8 | Chest |
| 26-12 | 508.8 | 626.2 | Sternum |
| 65-1 | 606.6 | 645.8 | Chest |
| 65-2 | 821.9 | 645.8 | Sternum |
| 65-3 | 673.2 | 665.4 | Chest |
| 65-4 | 782.8 | 743.6 | Chest |
| 65-5 | 743.6 | 567.5 | Abdomen |
| 65-6 | 645.8 | 802.3 | Abdomen |
| 9-3 | 626.2 | 508.8 | Chest |
| Average | 674.30 | 638.79 | |
| Standard Deviation | 88.07 | 104.01 | |

The similarity of the primary frequencies provided a proof-of-concept for ballistic impact detection. The primary frequency range (489-822 Hz) of the impact signature is much higher than what is typically generated in the body during routine activity. Running, jumping and even blunt thumps to the body elicit only a typical 100 Hertz tissue displacement frequency that was also seen in the ballistic signature analysis.

Figure 18:
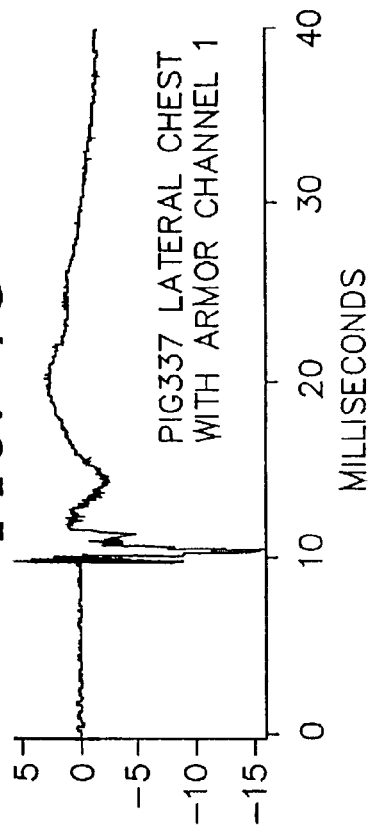
FIG. 18 shows a lateral chest hit with body armor signature.

A multi-protocol research plan was developed to compare impact signatures across models with those from humans. For this purpose, a commercial paintball rifle was chosen to deliver standardized impacts. Paintballs offered a socially acceptable method of delivering an impact to human volunteers for comparison to similar swine and human cadaver impacts. It was thought that similarity of low velocity impact signatures with that of humans would build a strong case for the necessary high velocity impacts in that model. Four swine weighing from 48 to 75 kg were impacted in four locations each (sternum, lateral chest, abdomen and hind leg), with and without body armor while under anesthesia. Five paintballs were fired at each location for a total of forty shots per pig (4 locations×5 shots with body armor plus 4 locations×5 shots without body armor). Eight Piezo-film sensors were attached to the pig's back in two columns of four, symmetrical about the spine. The armor/non-armor portions of the testing were randomized, as was the shot order in each portion. However, all 20 shots were fired before changing into or out of the body armor. Similarly, all five shots per position were fired before changing to a different impact location. The animals were fitted with older versions of aviation flak jackets for these tests. A total of 1280 impacts recordings were acquired (4 pigs×4 locations×2 body armor×5 shots×8 sensors). Analysis revealed that, while impacts were discernable for almost every sensor and every shot, many of the impact recordings were too low in amplitude and not similar to the non-lethal impacts seen in the proof-of-concept work. Load cell analyses of the paintball impacts show forces that are 25 times less than the solid steel balls used in the non-lethal phase. Calculated values for the non-lethal projectiles range from 46 to 66 Joules, at the velocities (250-300 ft/sec) used in the protocol. Paintball impacts can be calculated at 8 Joules (using 3 grams and 250 ft/sec). However, this calculation does not consider the work expended as the paintball breaks upon impact. Paintball impacts were measured using a load cell at 2 Joules. It is suspected that the difference in the force of the impacts does not cause the characteristic impact signatures of the non-lethal wounding studies. A typical lateral chest with armor signature is shown in FIG. 18. The signature in FIG. 18 can be broken into three separate sections: the pre-impact section from 0 to 9 milliseconds; the impact section from 9 to 12 milliseconds; and the tissue displacement section from 12 milliseconds on. With no way of determining the actual time of impact of these recordings, the pre-impact section of the signatures is considered to represent the response from the air blast of the paintball rifle when fired. The impact section corresponds to the shock wave section in the non-lethal wounding signatures. Due to the diminished force of impact of the paintball, the impact section duration is shorter than the non-lethal signatures. The diminished force of impact also causes the amplitudes of the tissue displacement wave to be much lower than the non-lethal recordings. It should be noted that a plywood baffle was used in the non-lethal wounding protocol to dissipate the air blast from the gun to prevent the chronographs from prematurely actuating. No indication of the air blast is evident in those recordings.

Figure 19:
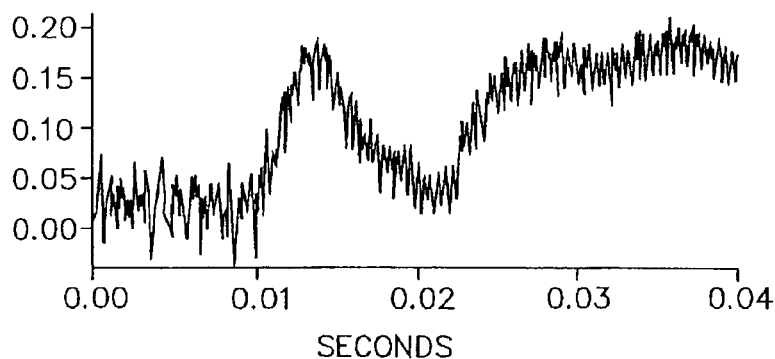
FIG. 19 shows a response for a sensor registering shot locations in the abdomen, sternum and hind limb.

FIG. 19 shows a typical response for all but the closest sensors for shot locations in the abdomen, sternum and hind limb. The tissue displacement phase of the signal is present albeit very low in amplitude, but no discernable shock component of the signal is present. It is not surprising that the high frequency 'shock' components are lost over time and distance as the body's elastic and dampening nature acts to filter higher frequencies faster.

Figure 20:
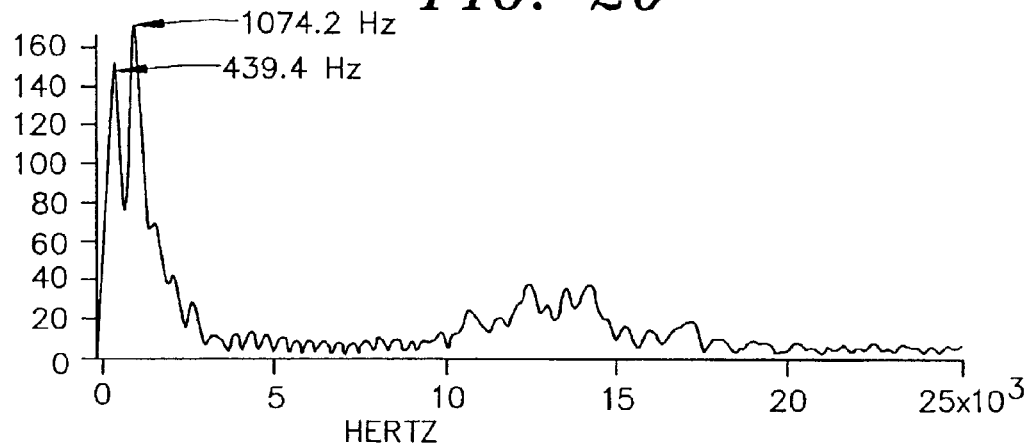
FIG. 20 shows a Fast Fourier Transform for the shock wave portion of the signal shown in FIG. 18.

Signals from all sensors were digitally recorded at 50,000 samples per second on each channel with a 10,000 hertz anti-aliasing filter. Analysis of the lateral chest shots of the pig (both armor and non-armor) revealed that the predominant shock frequencies occurred in the range of 300 to 700 Hz. Fast Fourier Transforms were performed on the shock section of each signature. The first 120 points of the shock section was zero-padded to 1024 points. The FFT returned 512 frequency coefficients over 25,000 Hertz range for a resolution of 48.8 Hertz per coefficient. The top two frequencies were recorded based on amplitude for each FFT. FIG. 20 shows the FFT for the shock wave portion of the signal shown in FIG. 18. It was quite common to see the double peaks shown in FIG. 20. These peaks are considered to be harmonics.

Table 3 shows average sensor reading for five shots at a lateral chest location while wearing body armor. In the cases where there was no top frequency in the 300-1000 Hertz range, the most significant peak in that range was selected and the amplitude noted.

TABLE 3

| | Pig ID | | | | | | | | Totals | |
| --- | --- | --- | --- | --- | --- | --- | --- | --- | --- | --- |
| | P337 | | P377 | | P378 | | P379 | | Average | Average |
| | Frequency | Amplitude | Frequency | Amplitude | Frequency | Amplitude | Frequency | Amplitude | Frequency | Amplitude |
| Sensor 1 | | | | | | | | | | |
| Avg | 434.26 | 141.50 | 454.02 | 4.70 | 600.48 | 272.13 | 400.08 | 254.96 | 472.21 | 168.32 |
| SD | 47.10 | 34.12 | 139.89 | 1.38 | 47.69 | 12.58 | 47.70 | 31.39 | 108.21 | 111.95 |
| Sensor 2 | | | | | | | | | | |
| Avg | 649.28 | 75.10 | 512.62 | 89.04 | 419.76 | 531.20 | 458.64 | 236.97 | 510.08 | 233.08 |
| SD | 180.79 | 5.42 | 48.70 | 12.54 | 20.51 | 22.36 | 60.76 | 17.56 | 127.24 | 188.76 |
| Sensor 3 | | | | | | | | | | |
| Avg | 429.32 | 126.24 | 497.88 | 151.94 | 473.38 | 259.58 | 331.88 | 163.10 | 433.12 | 175.22 |
| SD | 47.48 | 26.64 | 264.22 | 35.99 | 95.37 | 43.07 | 13.58 | 37.38 | 146.14 | 61.58 |
| Sensor 4 | | | | | | | | | | |
| Avg | 458.64 | 6.09 | 419.58 | 23.52 | 590.56 | 15.99 | 493.10 | 50.43 | 490.47 | 24.01 |
| SD | 95.31 | 2.08 | 43.84 | 7.42 | 179.16 | 3.18 | 55.52 | 3.34 | 118.11 | 17.38 |
| Sensor 5 | | | | | | | | | | |
| Avg | | | 385.64 | 44.08 | | | | | | |
| SD | | | 36.25 | 21.90 | | | | | | |
| Sensor 6 | | | | | | | | | | |
| Avg | | | 522.22 | 175.26 | | | | | | |
| SD | | | 27.75 | 60.16 | | | | | | |

The location of all lateral chest shots was on the right side approximately equal distance from two sensors. The snug fit of the body armor stabilizes the sensors and their response. To this end, data recorded in connection with armored protection were more consistent than the unarmored data. Table 4 shows the results of the lateral chest shots with body armor, comparable to the live animal impacts summarized in Table 3. Immediately noticeable in the cadaver impacts was the lack of analyzable signatures in channels 2 and 4 in some of the animals. These are the sensors on the far side (non-shot side). However, overall the top frequencies are very comparable those of the live impacts. While the frequencies are remarkably similar, the amplitude of the cadaver signals is dramatically lower across all four sensors. Signal strength in the live animals ranged from 160 to 230 (except for sensor 4) while signals in the cadavers were markedly lower; the closest sensor registering an average of 65 and sensors 2 and 3 registering 26 and 24, respectively. Sensor 4 is again understandable lower than the other sensors as it is the farthest from the shot in both scenarios.

Figure 21:
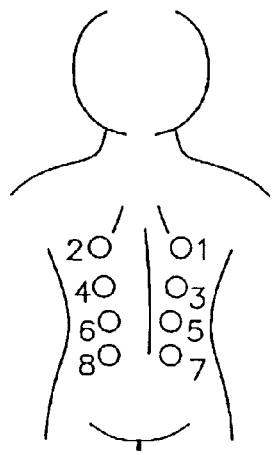
FIG. 21 shows the location of sensors placed on the back of a subject.

(opposite arm and opposite thigh) while not wearing the armor. Sensors were placed on the back of the subjects and fixed with adhesive tape similar to the pigs as shown in FIG. 21. Subjects wore jacket-style NATO body armor for this test.

Figure 22:
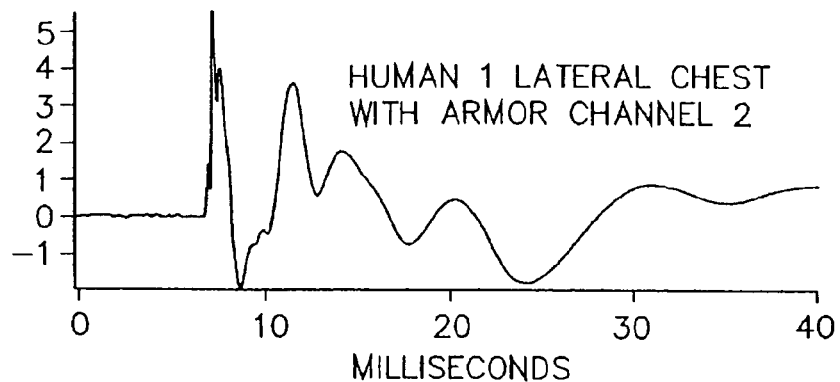
FIG. 22 shows a representative left lateral chest impact with body armor from signal sensor 2 as shown in FIG. 21.

In general, numerous human impact locations were analyzed and FFT data from eight, impact locations were computed. FIG. 22 shows a representative left lateral chest impact with body armor signal from sensor 2. It should be noted that the small pre-impact waves that were visible on the swine recordings are not visible in the human recordings. As previously stated, these small waves are believed to be artifact from the air blast of the gun. Since the human subjects stand behind protective plywood, it seems logical that the air blast is dissipated. The human impact signature in FIG. 22 prevents

TABLE 4

| | Pig ID | | | | | | | | Totals | |
| | P337 | | P377 | | P378 | | P379 | | Average | Average |
| | Frequency | Amplitude | Frequency | Amplitude | Frequency | Amplitude | Frequency | Amplitude | Frequency | Amplitude |
|---|---|---|---|---|---|---|---|---|---|---|
| Sensor 1 | | | | | | | | | | |
| Avg | 390.46 | 63.14 | 527.0 | 71.7 | 429.7 | 94.2 | 424.6 | 31.7 | 442.9 | 65.2 |
| SD | 71.0 | 24.0 | 47.7 | 4.9 | 21.9 | 8.4 | 50.7 | 11.0 | 70.0 | 26.4 |
| Sensor 2 | | | | | | | | | | |
| Avg | 468.4 | 51.6 | 615.1 | 9.1 | 473.4 | 17.0 | | | 519.0 | 25.9 |
| SD | 85.2 | 35.4 | 86.9 | 2.3 | 27.8 | 4.1 | | | 97.0 | 27.0 |
| Sensor 3 | | | | | | | | | | |
| Avg | 541.8 | 2.0 | 444.3 | 42.8 | 400.2 | 10.0 | 624.7 | 42.1 | 502.7 | 24.3 |
| SD | 263.6 | 0.8 | 10.7 | 22.4 | 50.6 | 7.5 | 58.9 | 29.9 | 154.6 | 25.8 |
| Sensor 4 | | | | | | | | | | |
| Avg | | | 546.7 | 4.0 | 395.3 | 3.1 | 748.4 | 3.5 | 535.0 | 3.5 |
| SD | | | 27.9 | 0.2 | 52.9 | 0.9 | 13.9 | 0.2 | 144.2 | 0.7 |

Figure 23:
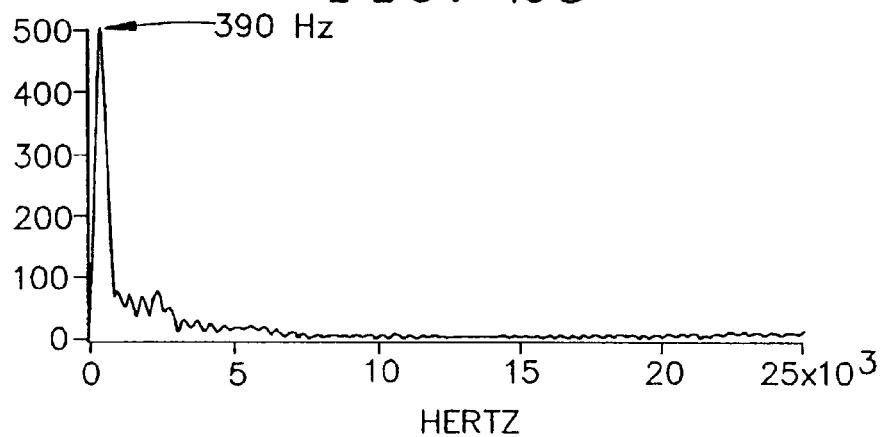
FIG. 23 shows the FFT performed on the impact shown in FIG. 22.

Three human test subjects volunteered for the paintball impact testing. Each subject received eight impacts, four with body armor and four without body armor. Subjects received impacts in the abdomen, lateral chest with and without the armor and received two extremity shots (one arm and one thigh) wearing armor and then two more extremity shots shock and tissue deformation components corresponding to the swine recordings. FIG. 23 shows the FFT performed on the impact shown in FIG. 22. FFT analysis on the shock portion of the recordings similar to those performed on the swine impact recordings for the lateral chest impacts are summarized in Table 5.

TABLE 5

| | Subject 1 | | Subject 2 | | Subject 3 | | Average | |
| Sensor | Frequency | Amplitude | Frequency | Amplitude | Frequency | Amplitude | Frequency | Amplitude |
|---|---|---|---|---|---|---|---|---|
| 1 | 341.8 | 3.6 | 537.1 | 6.3 | 341.8 | 7 | 406.90 | 5.63 |
| 2 | 390.6 | 501.5 | 488.3 | 323.3 | — | — | 439.45 | 412.40 |
| 3 | 390.6 | 22.2 | 488.3 | 60.9 | 609.9 | 12.1 | 496.27 | 31.73 |
| 4 | 439.4 | 70.5 | 512.3 | 273.7 | — | — | 475.85 | 172.10 |
| 5 | 439.5 | 29.2 | 365.8 | 114.2 | 365.8 | 12.2 | 390.37 | 51.87 |
| 6 | 365.8 | 57.5 | 585.9 | 321.4 | 488.3 | 11.6 | 480.00 | 130.17 |
| 7 | 488.3 | 173.7 | 414.6 | 163.9 | 341.8 | 40.2 | 414.90 | 125.93 |
| 8 | 439.4 | 215.4 | 390.6 | 259.7 | 390.6 | 10.5 | 406.87 | 161.87 |

The frequencies noted in Table 5 represent the top frequency peaks. Overall to this point, the peak frequencies of the human subject correlate well with the swine frequencies. The average frequency for the human lateral chest shots with body armor is 437.1 Hertz with a standard deviation of 78.6 (n=22). The average frequency for the swine lateral chest shots with body armor is 471.1 Hertz with a standard deviation of 122.0 (n=90).

Similarities between the low impact swine and low impact human signatures provided the needed impetus to perform high velocity swine impacts. A protocol was written to perform a limited number of shots using two caliber bullets (7.62 M80 ball and 5.56 M855 ball), four locations (sternum, lateral chest, abdomen and hind limb) and three velocities (2800 ft/sec, 2300 ft/sec and 1300 ft/sec). The impact schedule is shown in Table 6. It was important to test a combination of threats facing the soldier today. Given that resources were limited, certain tradeoffs were made. The velocities were chosen to reflect an AK47 muzzle velocity (2800 ft/sec), an approximate 200 yard rifle engagement (2300 ft/sec) and handgun velocity (1300 ft/sec).

TABLE 6

| Shot ID. | Location | Round | Armor | Velocity |
| --- | --- | --- | --- | --- |
| PHV-1 | Lat Chest | M80 Ball | Soft Armor | High |
| PHV-2 | Lat Chest | M80 Ball | Soft Armor | High |
| PHV-3 | Lat Chest | M80 Ball | Soft Armor | High |
| PHV-4 | Lat Chest | M80 Ball | Soft Armor | High |
| PHV-5 | Lat Chest | M80 Ball | Soft Armor | High |
| PHV-6 | Sternum | M80 Ball | Plate | High |
| PHV-7 | Sternum | M80 Ball | Plate | High |
| PHV-8 | Sternum | M80 Ball | Plate | High |
| PHV-9 | Sternum | M80 Ball | Plate | High |
| PHV-10 | Sternum | M80 Ball | Plate | High |
| PHV-11 | Abdomen | M80 Ball | Soft Armor | High |
| PHV-12 | Abdomen | M80 Ball | Soft Armor | High |
| PHV-13 | Abdomen | M80 Ball | Soft Armor | High |
| PHV-14 | Abdomen | M80 Ball | Soft Armor | High |
| PHV-15 | Abdomen | M80 Ball | Soft Armor | High |
| PHV-16 | Limb | M80 Ball | No Armor | High |
| PHV-17 | Limb | M80 Ball | No Armor | High |
| PHV-18 | Limb | M80 Ball | No Armor | High |
| PHV-19 | Limb | M80 Ball | No Armor | High |
| PHV-20 | Limb | M80 Ball | No Armor | High |
| PHV-21 | Lat Chest | M80 Ball | Soft Armor | Medium |
| PHV-22 | Lat Chest | M80 Ball | Soft Armor | Medium |
| PHV-23 | Lat Chest | M80 Ball | Soft Armor | Medium |
| PHV-24 | Lat Chest | M80 Ball | Soft Armor | Medium |
| PHV-25 | Lat Chest | M80 Ball | Soft Armor | Medium |
| PHV-26 | Sternum | M80 Ball | Plate | Medium |
| PHV-27 | Sternum | M80 Ball | Plate | Medium |
| PHV-28 | Sternum | M80 Ball | Plate | Medium |
| PHV-29 | Sternum | M80 Ball | Plate | Medium |
| PHV-30 | Sternum | M80 Ball | Plate | Medium |
| PHV-31 | Abdomen | M80 Ball | Soft Armor | Medium |
| PHV-32 | Abdomen | M80 Ball | Soft Armor | Medium |
| PHV-33 | Abdomen | M80 Ball | Soft Armor | Medium |
| PHV-34 | Abdomen | M80 Ball | Soft Armor | Medium |
| PHV-35 | Abdomen | M80 Ball | Soft Armor | Medium |
| PHV-36 | Limb | M80 Ball | No Armor | Medium |
| PHV-37 | Limb | M80 Ball | No Armor | Medium |
| PHV-38 | Limb | M80 Ball | No Armor | Medium |
| PHV-39 | Limb | M80 Ball | No Armor | Medium |
| PHV-40 | Limb | M80 Ball | No Armor | Medium |
| PHV-41 | Lat Chest | M80 Ball | Soft Armor | Low |
| PHV-42 | Lat Chest | M80 Ball | Soft Armor | Low |
| PHV-43 | Lat Chest | M80 Ball | Soft Armor | Low |
| PHV-44 | Lat Chest | M80 Ball | Soft Armor | Low |
| PHV-45 | Lat Chest | M80 Ball | Soft Armor | Low |
| PHV-46 | Sternum | M80 Ball | Plate | Low |
| PHV-47 | Sternum | M80 Ball | Plate | Low |
| PHV-48 | Sternum | M80 Ball | Plate | Low |
| PHV-49 | Sternum | M80 Ball | Plate | Low |
| PHV-50 | Sternum | M80 Ball | Plate | Low |
| PHV-51 | Abdomen | M80 Ball | Soft Armor | Low |
| PHV-52 | Abdomen | M80 Ball | Soft Armor | Low |
| PHV-53 | Abdomen | M80 Ball | Soft Armor | Low |
| PHV-54 | Abdomen | M80 Ball | Soft Armor | Low |
| PHV-55 | Abdomen | M80 Ball | Soft Armor | Low |
| PHV-56 | Limb | M80 Ball | No Armor | Low |
| PHV-57 | Limb | M80 Ball | No Armor | Low |
| PHV-58 | Limb | M80 Ball | No Armor | Low |
| PHV-59 | Limb | M80 Ball | No Armor | Low |
| PHV-60 | Limb | M80 Ball | No Armor | Low |
| PHV-61 | Lat Chest | M855 | Soft Armor | Medium |
| PHV-62 | Lat Chest | M855 | Soft Armor | Medium |
| PHV-63 | Lat Chest | M855 | Soft Armor | Medium |
| PHV-64 | Lat Chest | M855 | Soft Armor | Medium |
| PHV-65 | Lat Chest | M855 | Soft Armor | Medium |
| PHV-66 | Limb | M855 | No Armor | Medium |
| PHV-67 | Limb | M855 | No Armor | Medium |
| PHV-68 | Limb | M855 | No Armor | Medium |
| PHV-69 | Limb | M855 | No Armor | Medium |
| PHV-70 | Limb | M855 | No Armor | Medium |
| PHV-71 | Lat Chest | M855 | Soft Armor | Low |
| PHV-72 | Lat Chest | M855 | Soft Armor | Low |
| PHV-73 | Lat Chest | M855 | Soft Armor | Low |
| PHV-74 | Lat Chest | M855 | Soft Armor | Low |
| PHV-75 | Lat Chest | M855 | Soft Armor | Low |
| PHV-76 | Limb | M855 | No Armor | Low |
| PHV-77 | Limb | M855 | No Armor | Low |
| PHV-78 | Limb | M855 | No Armor | Low |
| PHV-79 | Limb | M855 | No Armor | Low |
| PHV-80 | Limb | M855 | No Armor | Low |

Figure 24:
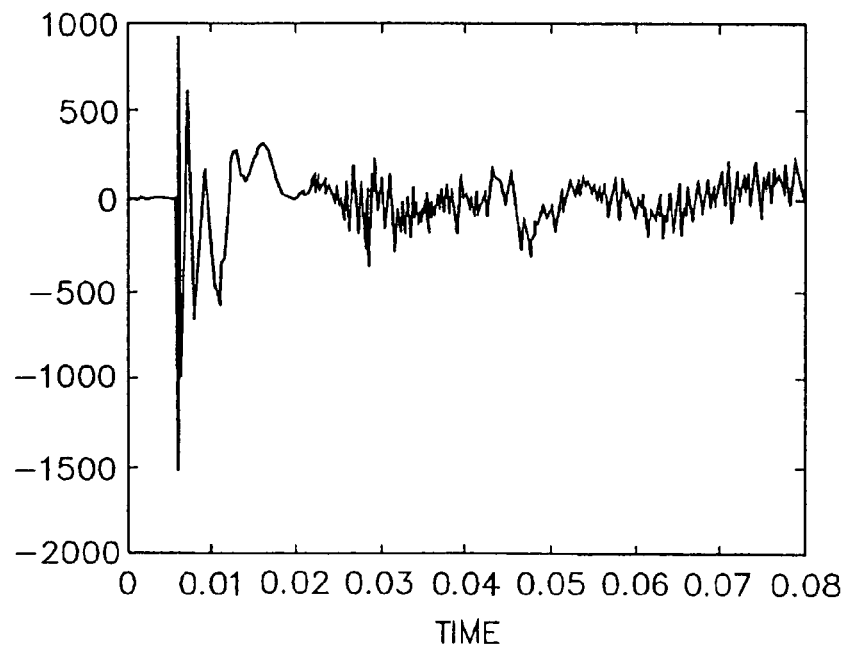
FIGS. 24 and 25 show typical impact signatures.
Figure 25:
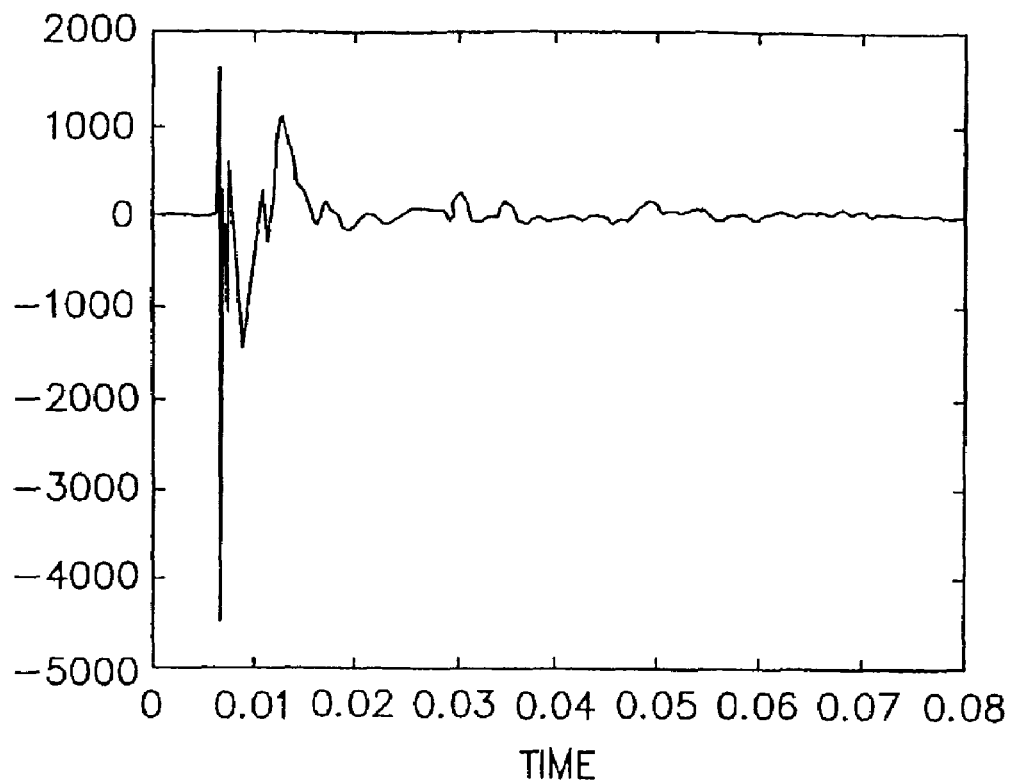

7.62 rounds are currently the most common small arms threat to US soldiers on the battlefield and are fired by various Soviet Block style weapons (e.g. AK-47, RPK, RPD, etc.). The M855 round (5.56 mm) is a standard NATO round and represents the trend of reducing the bullet caliber and total round weight to gain higher velocity and decrease soldier basic ammunition load weight. This smaller caliber provides information about smaller high-velocity fragmentation munitions impacts (e.g. howitzers, mortars, grenades, etc). The chosen locations reflect the desire to maintain consistency with the low velocity protocols. However, in this study, body armor was used for all impacts. The targeted population for the BIDS is the frontline combat soldier. Projected warfighter designs call for body armor. It was important in the low velocity impact study to relate back to the proof-of-concept work originally done without body armor. Therefore, low impact tests were conducted wearing body armor and without body armor. The high impact tests do not need to relate back to previous low impact tests since results from these high impact tests alone will be the basis for the BIDS circuitry. Interceptor body armor from Point Blank with SAPI and Gamma Plus ceramic plates were used for this study. Sternum shots were fired into the ceramic plates of the vest, abdomen shots were fired into the Kevlar outer tactical vest just below the ceramic plates, lateral chest shots were fired into the Kevlar outer tactical vest and hind limb shots were fired into the unprotected thigh of the animal. The ceramic plates, which are rated to protect against 7.62 rounds at 2800 ft/sec, defeated all rounds at all velocities, although permanent backface deformations of approximately 1 cm were created at the high velocities. The Kevlar outer tactical vest is rated to defeat handgun rounds; however, the high ogive of the rifle rounds allowed all rounds to penetrate the Kevlar. A pilot study was performed to determine if freshly euthanized animals could be used instead of live anesthetized animals. Lateral chest shots using 7.62 rounds at 2800 ft/sec from six live anesthetized animals were compared to animals that were euthanized minutes before the impact. As in previous experiments, eight sensors were placed equidistant about the spine in two columns of four. Unlike other experiments, these tests employed six newly design Piezo-film sensors as well as two of the older style bone conducting sensors. Unfortunately, the new sensors were not as responsive as the older bone conducting ones and have been left out of the analysis. The results from these tests will be from signatures recorded from the two bone conducting sensors. FIGS. 24 and 25 show typical impact signatures from form the pilot study. The graph on the left is a 2800 ft/sec 7.62 round left lateral chest impact from a live anesthetized animal. The graph on the right is the same parameters from a freshly euthanized animal.

Figure 26:
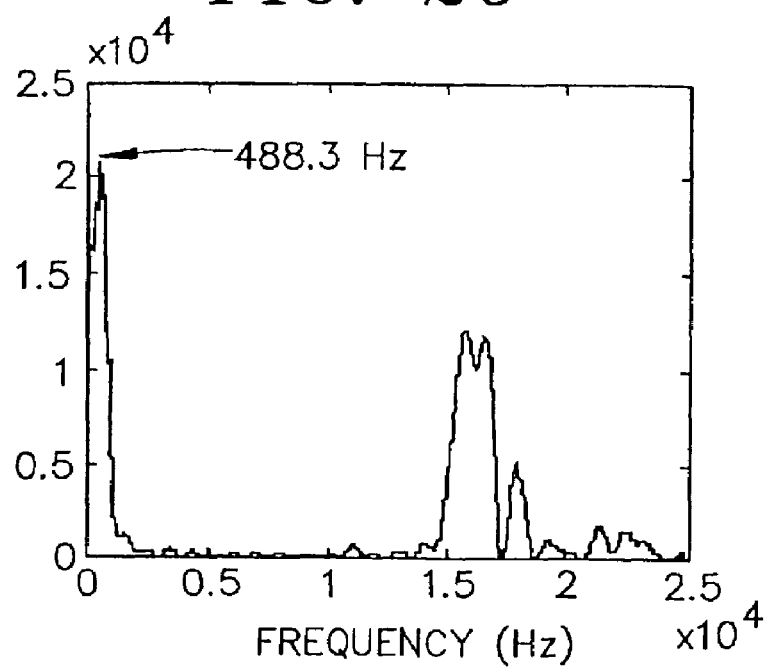
FIGS. 26 and 27 show the frequency spectrum of the impact signatures of FIGS. 24 and 25.
Figure 27:
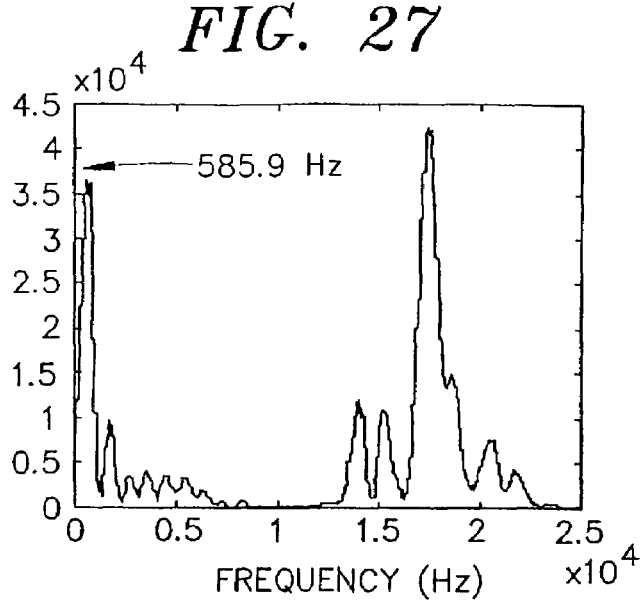

Similarly, FIGS. 26 and 27 show the frequency spectrum of the above impact signatures: live in FIG. 26 and freshly euthanized in FIG. 27. The FFTs below are 1024 point FFTs using 75 data points and zero-padding. The Y-axis is always in arbitrary units which can be compared between graphs in which similar processing has been performed. After completing the pilot study, the remaining animals were impacted directly after euthanasia. It should be noted that the sensor used in these recordings has a particular resonance at 17,000 Hz explaining the large frequency response in that area on the graphs in FIGS. 26 and 27. While there was some signal present in that frequency region, care must be used in characterizing the frequency response of the sensors as it affects the analysis of the impact signatures.

Figure 28:
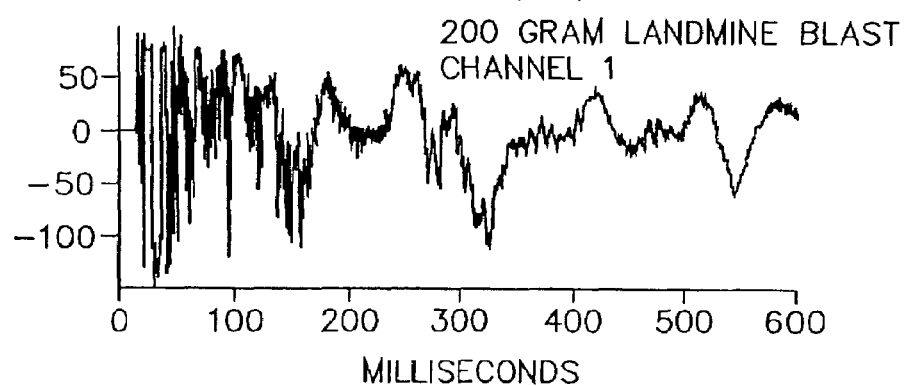
FIG. 28 shows a signal produced from a 200 gram landmine blast on channel 1.
Figure 29:
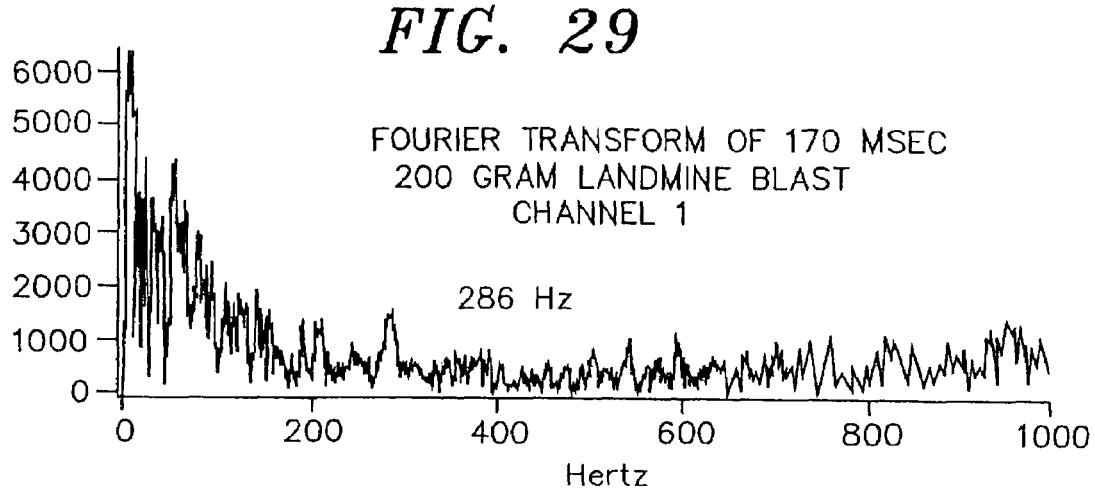
FIG. 29 shows the Fast Fourier Transform of the blast shown in FIG. 28.

Mine surrogates containing surrogates containing 100 and 200 grams of C4 explosive were used against cadavers with and without a blast suit. Sensors were affixed to the cadavers using superglue in the same configuration as FIG. 21. Signals were recorded at 50,000 samples per second on each channel. FIG. 28 shows the impact signal from a 200-gram blast with a blast suit. The subject's nose was 55 centimeters (measured radially) from the center of the mine surrogate. The response from the sensor seems to be that of a second-order system in response to a step function. A second order system consists of a mass, a spring and a dashpot (shock absorber). FIG. 28 shows a longer duration event lasting well beyond 600 milliseconds. Examination of the recording indicates higher frequency components for the first 150 milliseconds and slower frequencies after 150 milliseconds. It is likely that part of the slower frequency waves are made up of the tissue deformation waves. An FFT on the first 170 milliseconds of the blast is shown in FIG. 29. Much of the response to this type of blast is in the lower frequencies, less than 200 Hertz. This seems to indicate that the surface of the body couples with the primary low frequency blast wave.

Figure 30:
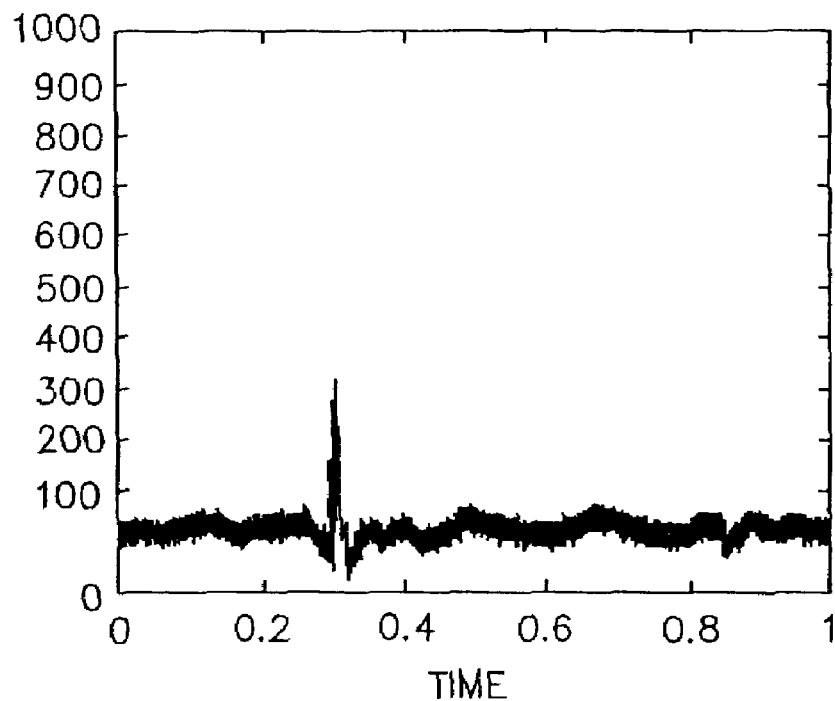
FIG. 30 shows the resulting signal from a 30-inch jump.
Figure 31:
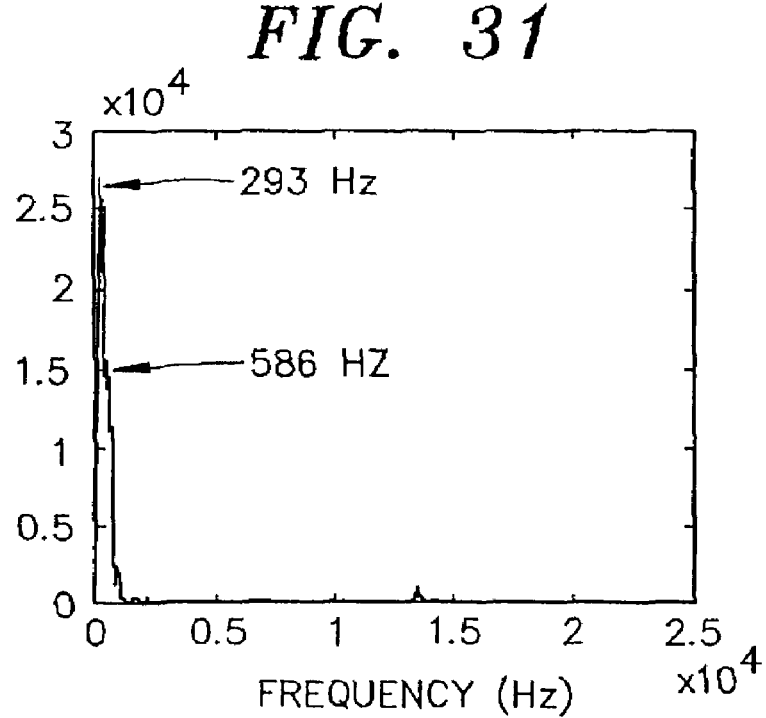
FIG. 31 shows a frequency domain spectrum produced by a Fast Fourier Transform of the 30-inch jump.

Data was also acquired for simulated normal activity to determine key characteristics of signals from running, hopping and a significant jolt. Human data was collected while the subject ran and hopped in place. The jolt signature resulted in a jump off a 30 inch table. FIG. 30 is the resultant signal from the 30 inch jump. FIG. 31 is the frequency domain spectrum produced by the FFT. The frequency spectrum shows that this jolt to the body produces two significant frequencies: a larger amplitude component at 293 Hertz and a smaller but significant frequency at 586 Hertz. This latter frequency is in the range produced by the bullet impacts. Of the three 'normal' recordings, only the big jump proved to contain frequencies in the range of those produced by the bullet impacts.

Figure 32:
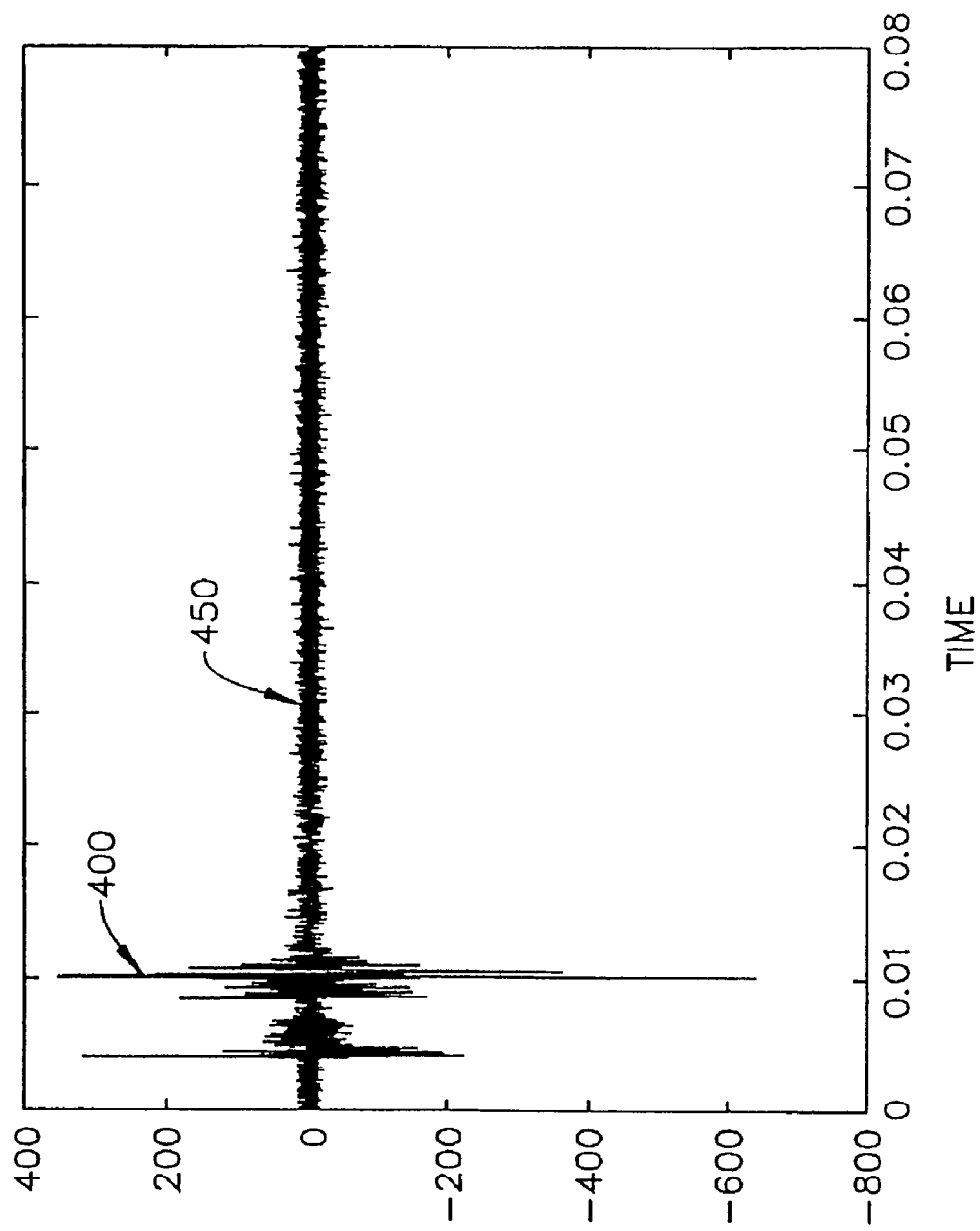
FIG. 32 shows a comparison of two signals filtered with a 3-pole 5,000 Hertz high pass filter.

Bench testing of the BIDS circuit included converting the digital impact signatures in analog voltages and feeding them through the circuit. The impact threshold settings were set so as to discriminate between the swine impacts and the normal human movement signatures. Setting the threshold is somewhat arbitrary since the voltage at that point is dependent upon the initial amplification from the input amplifier. More important is the relative voltage levels between the smallest detectable impact and the largest normal movement signal. FIG. 32 shows a comparison of two signals that have been filtered using the 3 pole 5000 Hertz high pass filter in the BIDS circuit. The first trace 400 is the time domain signal from a hind limb, 5.56 caliber impact at 1300 ft/sec; the second trace 450 is the time domain signal from the big jump in FIG. 30. FIG. 32 shows the ability to easily discriminate the weakest bullet impact recorded from the strongest 'normal' activity recording.

Although described with reference to preferred embodiments of and tests conducted in connection with the invention, it should be readily understood that various changes and/or modifications could be made to the invention without departing from the spirit thereof. For example, different types of signal processing circuitry for determining location of impacts or a target are shown in U.S. Pat. No. 4,349,728 which is incorporated herein by reference. Certainly, other logic elements could be used in the BIDS system without departing from the scope of the invention. In general, it is important that the sensor system of the invention can be used to detect, verify and locate a ballistic impact on a body, particularly an impact which causes an injury to the body. Detection and location information can be transmitted to a remote location, with this information being potentially used to enhance the ability to appropriately respond to counter the injury. In any case, the invention is only intended to be limited by the scope of the following claims.

We claim:

1. A wearable ballistic impact detection system for detecting impacts to a body of an individual comprising:
    a plurality of spaced sensors adapted to be supported by the body for detecting ballistic impact vibrations which are converted into electrical signals; and
    electronic logic circuitry receiving the electrical signals and determining both an occurrence of a ballistic impact to the body at a location spaced from the plurality of sensors and the location of the impact, wherein the electronic logic circuitry comprises:
    at least one filter electrically connected to said plurality of sensors for receiving the electrical signals and transmitting a filtered electrical signal of interest; and
    a group of electronic components for determining if the signal of interest has frequency and amplitude characteristics of an impact that causes injury to the body.

2. The system of claim 1, wherein the electronic logic circuitry further comprises: an input buffer amplifier.

3. The system of claim 1, wherein the at least one filter constitutes a high pass filter.

4. The system of claim 1, wherein the group of electronic components includes a rectifier for rectifying the signal of interest received from the at least one filter.

5. The system of claim 1, wherein said group of electronic components includes a low pass filter.

6. The system of claim 1, wherein said group of electronic components includes a peak hold circuit for measuring a peak voltage from the electrical signal of interest.

7. The system of claim 1, wherein the electronic logic circuitry further comprises: a logarithmic amplifier.

8. The system of claim 1, further comprising: an article of clothing supporting the plurality of sensors at spaced locations on the body.

9. The system of claim 8, wherein the article of clothing constitutes body armor.

10. The system of claim 1, wherein the impact vibrations have frequencies in an audible range.

11. The system of claim 1, further comprising: a transmitter for transmitting information about the impact to a remote location.

12. The system of claim 1, wherein the electronic logic circuitry determines the location of the impact based on a peak voltage received from the plurality of sensors.

13. The system of claim 1, wherein at least one of the plurality of sensors constitutes a piezo-film sensing element.

14. A wearable ballistic impact detection system for detecting impacts to a body of an individual comprising:
  sensor means, adapted to be supported on the body, for detecting impact vibrations which are converted into electrical signals; and
  logic means for receiving the electrical signals and determining both an occurrence of a ballistic impact to the body at a location spaced from the plurality of sensors and the location of the impact, wherein the logic means comprises:
  at least one filter electrically connected to said plurality of sensors for receiving the electrical signals and transmitting a filtered electrical signal of interest; and
  a group of electronic components for determining if the signal of interest has frequency and amplitude characteristics of an impact that causes injury to the body.

15. A method of detecting ballistic impacts to a body of an individual comprising:
  detecting vibrations caused by a ballistic impact through a plurality of spaced sensors supported by the body;
  converting the vibrations into electrical signals; and
  analyzing the electrical signals to determine both an occurrence of a ballistic impact to the body at a location spaced from the plurality of sensors and the location of the impact, wherein analyzing the electrical signals includes:
  filtering the electrical signals with at least one filter so as to pass only filtered electrical signals within a frequency range of interest;
  obtaining a peak voltage value in the desired frequency range of interest; and
  determining the occurrence and location of the impact by comparing the peak voltage value to a reference voltage value.

16. The method of claim 15, wherein analyzing the electrical signals further includes:
  rectifying the filtered electrical signals to produce rectified signals;
  compressing the rectified signals to produce compressed signals within the frequency range of interest;
  processing the compressed signals to obtain the peak voltage value.

17. The method of claim 15, further comprising:
  transmitting information about the impact to a remote location.

18. The method of claim 15, further comprising: supporting the plurality of sensors at spaced locations on body armor worn by the individual.

* * * * *